US011426586B2

(12) United States Patent
Perryman et al.

(10) Patent No.: US 11,426,586 B2
(45) Date of Patent: Aug. 30, 2022

(54) CIRCUIT FOR AN IMPLANTABLE DEVICE

(71) Applicant: Stimwave Technologies Incorporated, Pompano Beach, FL (US)

(72) Inventors: Laura Tyler Perryman, Pompano Beach, FL (US); Chad David Andresen, Miami Beach, FL (US); Bertan Bakkaloglu, Scottsdale, AZ (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 369 days.

(21) Appl. No.: 16/674,486

(22) Filed: Nov. 5, 2019

(65) Prior Publication Data

US 2020/0376275 A1    Dec. 3, 2020

Related U.S. Application Data

(63) Continuation of application No. 15/383,646, filed on Dec. 19, 2016, now Pat. No. 10,493,279, which is a
(Continued)

(51) Int. Cl.
*A61N 1/36*    (2006.01)
*H02J 50/27*    (2016.01)
(Continued)

(52) U.S. Cl.
CPC ....... *A61N 1/36125* (2013.01); *A61N 1/3787* (2013.01); *A61N 1/37223* (2013.01);
(Continued)

(58) Field of Classification Search
None
See application file for complete search history.

(56) References Cited

U.S. PATENT DOCUMENTS 4,612,934 A * 9/1986 Borkan .............. A61N 1/36185
607/40
5,735,887 A    4/1998 Barreras, Sr. et al.
(Continued)

FOREIGN PATENT DOCUMENTS

CN    102120060    3/2011
CN    103796715    4/2014
(Continued)

OTHER PUBLICATIONS

Extended European Search Report in European Appln. No. 20200626.8, dated Feb. 11, 2021, 8 pages.
(Continued)

*Primary Examiner* — Michael W Kahelin
(74) *Attorney, Agent, or Firm* — Fish & Richardson P.C.

(57) ABSTRACT

An integrated circuit includes: a radio-frequency (RF) to direct current (DC) rectifying circuit coupled to one or more antenna on an implantable wirelessly powered device, the rectifying circuit configured to: rectify an input RF signal received at the one or more antennas and from an external controller through electric radiative coupling; and extract DC electric power and configuration data from the input RF signal; a logic control circuit connected to the rectifying circuit and a driving circuit, the logic control circuit configured to: generate a current for the driving circuit solely using the extracted DC electrical power; in accordance with the extracted configuration data, set polarity state information for each electrode; and a driving circuit coupled to one or more electrode, the driving circuit comprising current mirrors and being configured to: steer, to each electrode and via the current mirrors, a stimulating current solely from the generated current.

19 Claims, 19 Drawing Sheets

Related U.S. Application Data continuation of application No. 14/796,067, filed on Jul. 10, 2015, now Pat. No. 9,522,270.

(60) Provisional application No. 62/022,768, filed on Jul. 10, 2014.

(51) Int. Cl.

| | | |
|---|---|---|
| *H02J 50/23* | (2016.01) | |
| *H02J 7/02* | (2016.01) | |
| *H02J 50/20* | (2016.01) | |
| *A61N 1/372* | (2006.01) | |
| *A61N 1/378* | (2006.01) | |

(52) U.S. Cl.
CPC .............. *H02J 7/025* (2013.01); *H02J 50/20* (2016.02); *H02J 50/23* (2016.02); *H02J 50/27* (2016.02)

(56) References Cited

U.S. PATENT DOCUMENTS

| | | | |
|---|---|---|---|
| 5,941,906 | A | 8/1999 | Barreras, Sr. et al. |
| 7,444,181 | B2 | 10/2008 | Shi et al. |
| 2007/0032827 | A1 | 2/2007 | Katims |
| 2007/0067004 | A1 | 3/2007 | Boveja et al. |
| 2007/0135868 | A1* | 6/2007 | Shi .................... A61N 1/36071 607/62 |
| 2010/0125315 | A1 | 5/2010 | Parramon et al. |
| 2010/0280568 | A1 | 11/2010 | Bulkes et al. |
| 2011/0276103 | A1 | 11/2011 | Maile et al. |
| 2012/0283800 | A1* | 11/2012 | Perryman .............. G16H 20/30 607/60 |
| 2012/0330384 | A1 | 12/2012 | Perryman et al. |
| 2013/0066400 | A1 | 3/2013 | Perryman et al. |
| 2013/0184794 | A1 | 7/2013 | Feldman et al. |
| 2014/0051965 | A1 | 2/2014 | Zdeblick et al. |
| 2014/0088379 | A1 | 3/2014 | Lrazoqui et al. |
| 2015/0238764 | A1 | 8/2015 | Franke |
| 2017/0001003 | A1 | 1/2017 | Pivonka et al. |
| 2017/0095667 | A1 | 4/2017 | Yakovlev et al. |

FOREIGN PATENT DOCUMENTS

| | | |
|---|---|---|
| WO | WO 2001/089629 | 11/2001 |
| WO | WO 2012/103519 | 8/2012 |
| WO | WO 2012/138782 | 10/2012 |
| WO | WO 2013/019757 | 2/2013 |
| WO | WO 2013/025632 | 2/2013 |
| WO | WO 2013/040549 | 3/2013 |

OTHER PUBLICATIONS

Extended European Search Report in European Application No. 15818386.3, dated May 3, 2018, 7 pages.
EP Office Action in European Appln. No. 15818386.3, dated Dec. 6, 2019, 6 pages.
International Search Report and Written Opinion in International Application No. PCT/US2015/40033, dated Oct. 6, 2015, 7 pages.
PCT International Preliminary Report in International Appln. No. PCT/US2015/40033, dated Jan. 10, 2017, 6 pages.

* cited by examiner

CIRCUIT FOR AN IMPLANTABLE DEVICE

RELATED APPLICATIONS

This application is a continuation of U.S. application Ser. No. 15/383,646, filed Dec. 19, 2016, now U.S. Pat. No. 10,493,279, which is a continuation of U.S. application Ser. No. 14/796,067, filed Jul. 10, 2015, now U.S. Pat. No. 9,522,270, issued Dec. 20, 2016, which claims the benefit of U.S. Provisional Application Ser. No. 62/022,768, filed on Jul. 10, 2014. All of these prior applications are incorporated by reference in their entirety.

TECHNICAL FIELD

This application relates generally to implantable stimulators.

BACKGROUND

Modulation of excitable tissue in the body by electrical stimulation has become an important type of therapy for patients with chronic disabling conditions, including chronic pain, problems of movement initiation and control, involuntary movements, vascular insufficiency, heart arrhythmias and more. A variety of therapeutic intra-body electrical stimulation techniques can treat these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing. Typically, such devices utilize a subcutaneous battery operated implantable pulse generator (IPG) to provide power or other charge storage mechanisms.

SUMMARY

In one aspect, some implementations provide an integrated circuit for an implantable wirelessly powered device for implantation in a patient's body, the circuit including: a radio-frequency (RF) to direct current (DC) rectifying circuit coupled to one or more antenna on the implantable wirelessly powered device, the rectifying circuit configured to: rectify an input RF signal received at the one or more antennas and from an external controller through electric radiative coupling; and extract DC electric power and configuration data from the input RF signal; a driving circuit coupled to one or more electrode and configured to: steer a stimulating current to each electrode according to the extracted configuration data to modulate the neural tissue within the patient's body; and a logic control circuit connected to the rectifying circuit and the a driving circuit, the logic control circuit configured to: generate a current for the driving circuit solely using the extracted DC electrical power; in accordance with the extracted configuration data, set polarity state information for each electrode; and a driving circuit coupled to one or more electrode, the driving circuit comprising current mirrors and being configured to: steer, to each electrode and via the current mirrors, a stimulating current solely from the generated current to modulate neural tissue within the patient's body.

Implementations may include one or more of the following features. The driving circuit may include: a current source digital to analog circuit (DAC) and a current sink digital to analog circuit (DAC), the current source DAC and the current sink DAC being complementary to each other and both being mirrored connected to each electrode via the current mirrors wherein the stimulating current may be determined by a current mirror ratio and wherein the configuration data may include the current mirror ratio. The current mirror ratio may equal matches the number of electrodes.

The driving circuit may include: a switch bank configured to control a polarity state for each electrode. The driving circuit may include: a variable shunt resistor adapted to reduce a ripple on the electrode connected thereto when the stimulating current has just ended.

The integrated circuit may further include: a discharge delay timer to delay the onset of capacitors coupled to each of the electrodes.

The integrated circuit may further include: a power on reset (PoR) circuit to maintain default state information for each electrode and default parameters for the stimulating current for each electrode, the PoR circuit configured to be trigged on by a rising edge and turned off by a falling edge.

The integrated circuit may further include: one or more address control bits, configurable as a logic address of the implantable device wirelessly powered by the extracted electric power. The integrated circuit may further include a diode bridge.

The rectifying circuit may be coupled to a differential antenna on the implantable wirelessly powered device. The rectifying circuit may include: an amplitude modulation (AM) detection circuit to extract electric power and configuration data from the input signal.

The logic control circuit may include: a state machine to record state information for each electrode based on the extracted configuration data, the configuration data including polarity setting for each electrode. The logic control circuit may be further configured to set polarity state for each electrode during a communication initialization pulse. The logic control circuit may include a timer circuit to control a duration the generated current for the driving circuit.

BRIEF DESCRIPTION OF THE DRAWINGS

Like reference symbols in the various drawings indicate like elements.

DETAILED DESCRIPTION

Figure 1:
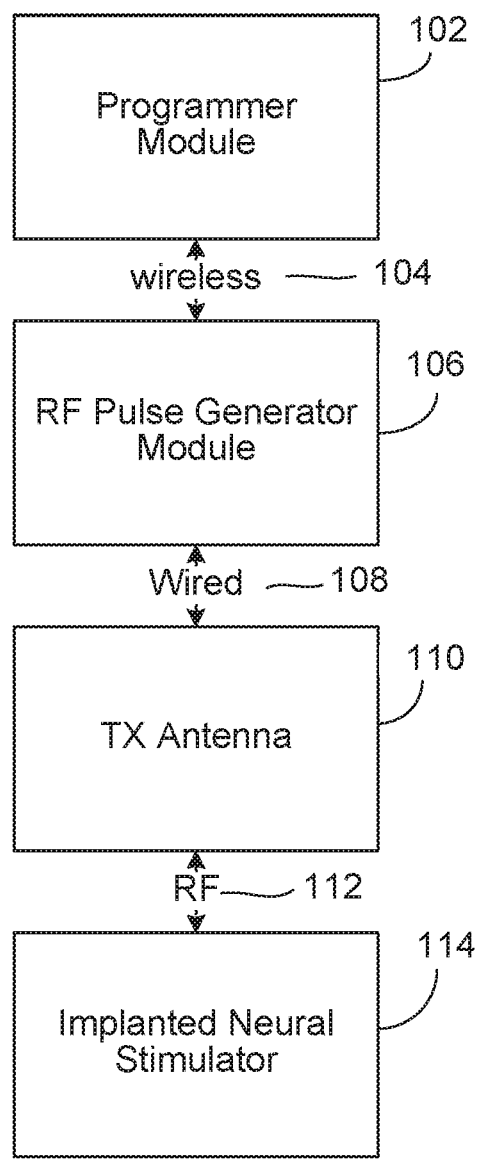
FIG. 1 depicts a high-level diagram of an example of a wireless stimulation system.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power a passive implanted wireless stimulator device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for frequency waveform and electrical energy rectification. The system may further comprise an external controller and antenna for transmitting radio frequency or microwave energy from an external source to the implantable stimulator device with neither cables nor inductive coupling to provide power.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil.

According to some implementations, the wireless implantable stimulator device includes an application-specific integrated circuit (ASIC) chip for interacting with an external controller and the electrodes contained within the device. The ASIC chip may harvest RF power from the received input signal sent from the external controller to power the wireless implantable stimulator device, including the ASIC chip. The ASIC chip may also extract waveform parameters from the received input signal and use such information to create electrical impulses for stimulating excitable tissues through the electrodes. In particular, the ASIC chip contains a current steering feature to mirror currents to each electrode with evenness while maintaining a compact chip size. Moreover, the ASIC chip may extract polarity setting information from the received input signal and use such information to set the polarity for electrode interfaces.

Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011 and PCT/US2012/55746, filed Sep. 15, 2011, the complete disclosures of which are incorporated by reference.

FIG. 1 depicts a high-level diagram of an example of a wireless stimulation system. The wireless stimulation system may include four major components, namely, a programmer module 102, a RF pulse generator module 106, a transmit (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless stimulator device 114. This input signal contains energy and may contain information encoding stimulus waveforms to be applied at the electrodes of the implanted wireless stimulator device 114. In some implementations, the power level of this input signal directly determines an applied amplitude (for example, power, current, or voltage) of the one or more electrical pulses created using the electrical energy contained in the input signal. Within the implanted wireless stimulator device 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 (or cylindrical wireless implantable stimulator device 1400 shown in FIGS. 14A and 14B, helical wireless implantable stimulator device 1900 shown in FIGS. 19A to 19C) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation current for maintaining effective neuronal activation, or, in some cases, the patient can manually adjust the output signals in an open loop control method.

Figure 2:
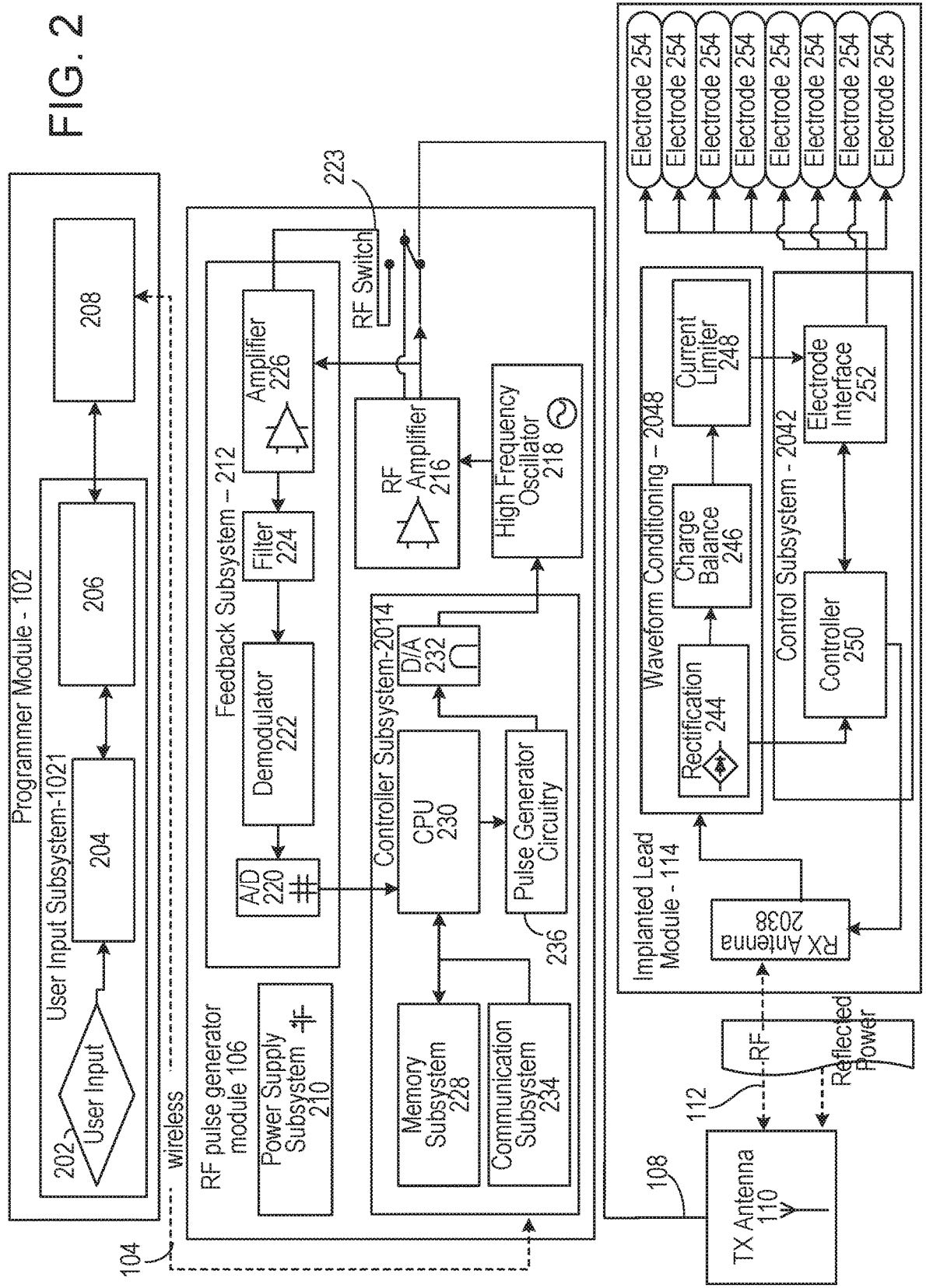
FIG. 2 depicts a detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

Stimulation Parameter Table 1
Pulse Amplitude: 0 to 20 mA
Pulse Frequency: 0 to 10000 Hz
Pulse Width: 0 to 2 ms The RF pulse generator module 106 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless stimulator device 114 to send instructions about the various operations of the wireless stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulator device 114), the RF switch 223 is set to send the forward power signal to feedback subsystem. During the off-cycle time (when an RF signal is not being transmitted to the wireless stimulator device 114), the RF switch 223 can change to a receiving mode in which the reflected RF energy and/or RF signals from the wireless stimulator device 114 are received to be analyzed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106 during its receive cycle. For example, the telemetry signal from the wireless stimulator device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 can generate telemetry data in real time, for example, at a rate of 8 Kbits per second. All feedback data received from the implanted stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulator device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T start and terminated at a time T final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulator device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units uC/cm$^2$. In order to avoid the irreversible electrochemical reactions such as pH change, electrode dissolution as well as tissue destruction, no net charge should appear at the electrode-electrolyte interface, and it is generally acceptable to have a charge density less than 30 uC/cm$^2$. Biphasic stimulating current pulses ensure that no net charge appears at the electrode after each stimulation cycle and the electrochemical processes are balanced to prevent net dc currents. The wireless stimulator device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment as disclosed herein, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulator device 114 may create a drive-waveform envelope that follows the envelope of the RF pulse received by the receiving dipole antenna(s) 238. In this case, the RF pulse generator module 106 can directly control the envelope of the drive waveform within the wireless stimulator device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulator device 114, such as controller 250. In the case of onboard control, the amplitude and timing may be specified or modified by data commands delivered from the pulse generator module 106.

Figure 3:
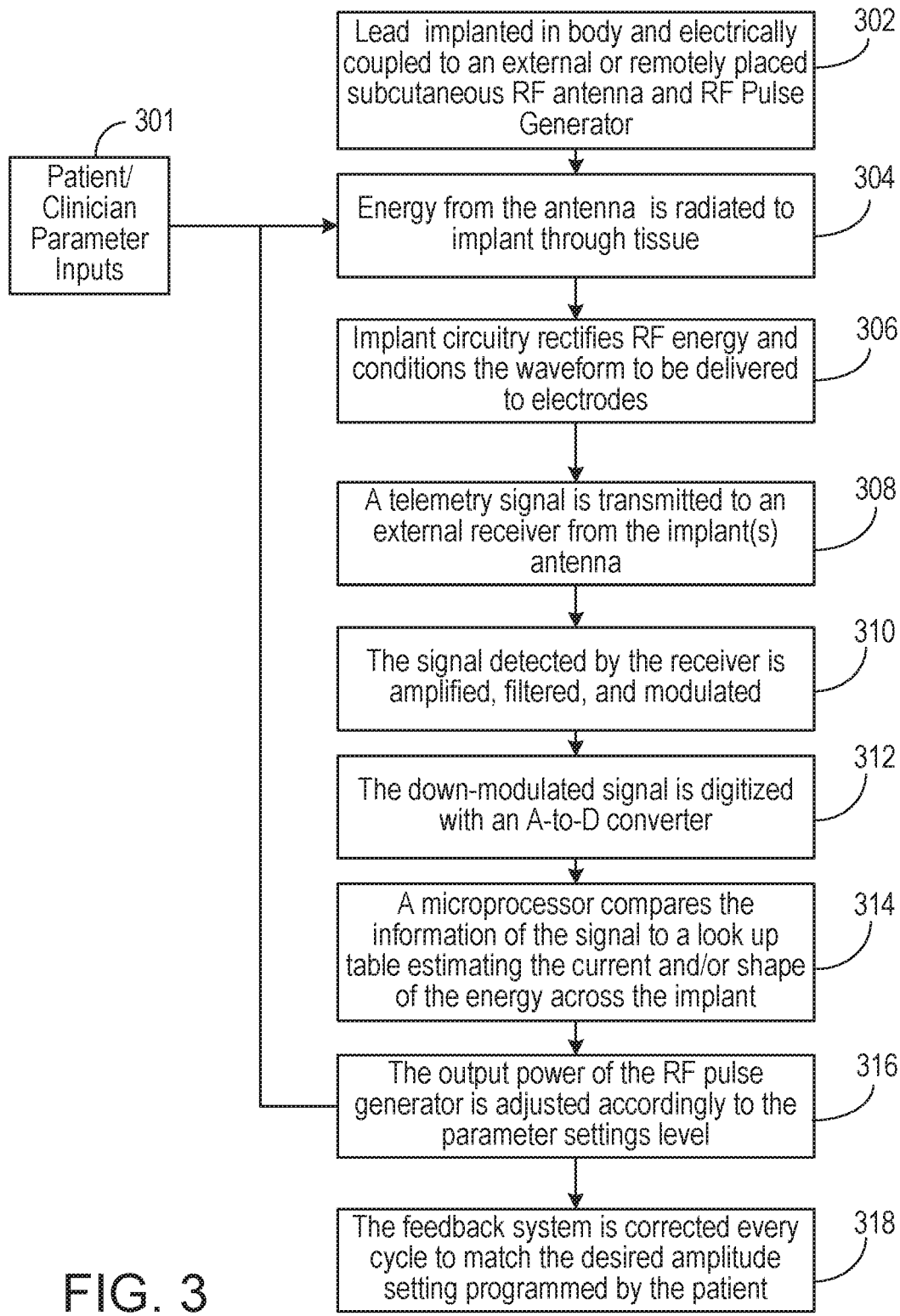
FIG. 3 is a flowchart showing an example of the operation of the wireless stimulation system.

FIG. 3 is a flowchart showing an example of an operation of a wireless neural stimulation system. In block 302, the wireless stimulator device 114 is implanted in proximity to nerve bundles and is coupled to the electric field produced by the TX antenna 110. That is, the pulse generator module 106 and the TX antenna 110 are positioned in such a way (for example, in proximity to the patient) that the TX antenna 110 is electrically radiatively coupled with the implanted RX antenna 238 of the wireless stimulator device 114. In certain implementations, both the antenna 110 and the RF pulse generator 106 are located subcutaneously. In other implementations, the antenna 110 and the RF pulse generator 106 are located external to the patient's body. In this case, the TX antenna 110 may be coupled directly to the patient's skin.

Energy from the RF pulse generator is radiated to the implanted wireless stimulator device 114 from the antenna 110 through tissue, as shown in block 304. The energy radiated may be controlled by the Patient/Clinician Parameter inputs in block 301. In some instances, the parameter settings can be adjusted in an open loop fashion by the patient or clinician, who would adjust the parameter inputs in block 301 to the system.

The implanted wireless stimulator device 114 uses the received energy to generate electrical pulses to be applied to the neural tissue through the electrodes 238. For instance, the wireless stimulator device 114 may contain circuitry that rectifies the received RF energy and conditions the waveform to charge balance the energy delivered to the electrodes to stimulate the targeted nerves or tissues, as shown in block 306. The implanted wireless stimulator device 114 communicates with the pulse generator 106 by using antenna 238 to send a telemetry signal, as shown in block 308. The telemetry signal may contain information about parameters of the electrical pulses applied to the electrodes, such as the impedance of the electrodes, whether the safe current limit has been reached, or the amplitude of the current that is presented to the tissue from the electrodes.

In block 310, the RF pulse generator 106 detects amplifies, filters and modulates the received telemetry signal using amplifier 226, filter 224, and demodulator 222, respectively. The A/D converter 230 then digitizes the resulting analog signal, as shown in 312. The digital telemetry signal is routed to CPU 230, which determines whether the parameters of the signal sent to the wireless stimulator device 114 need to be adjusted based on the digital telemetry signal. For instance, in block 314, the CPU 230 compares the information of the digital signal to a look-up table, which may indicate an appropriate change in stimulation parameters. The indicated change may be, for example, a change in the current level of the pulses applied to the electrodes. As a result, the CPU may change the output power of the signal sent to wireless stimulator device 114 so as to adjust the current applied by the electrodes 254, as shown in block 316.

Thus, for instance, the CPU 230 may adjust parameters of the signal sent to the wireless stimulator device 114 every cycle to match the desired current amplitude setting programmed by the patient, as shown in block 318. The status of the stimulator system may be sampled in real time at a rate of 8 Kbits per second of telemetry data. All feedback data received from the wireless stimulator device 114 can be maintained against time and sampled per minute to be stored for download or upload to a remote monitoring system accessible by the health care professional for trending and statistical correlations in block 318. If operated in an open loop fashion, the stimulator system operation may be reduced to just the functional elements shown in blocks 302, 304, 306, and 308, and the patient uses their judgment to adjust parameter settings rather than the closed looped feedback from the implanted device.

Figure 4:
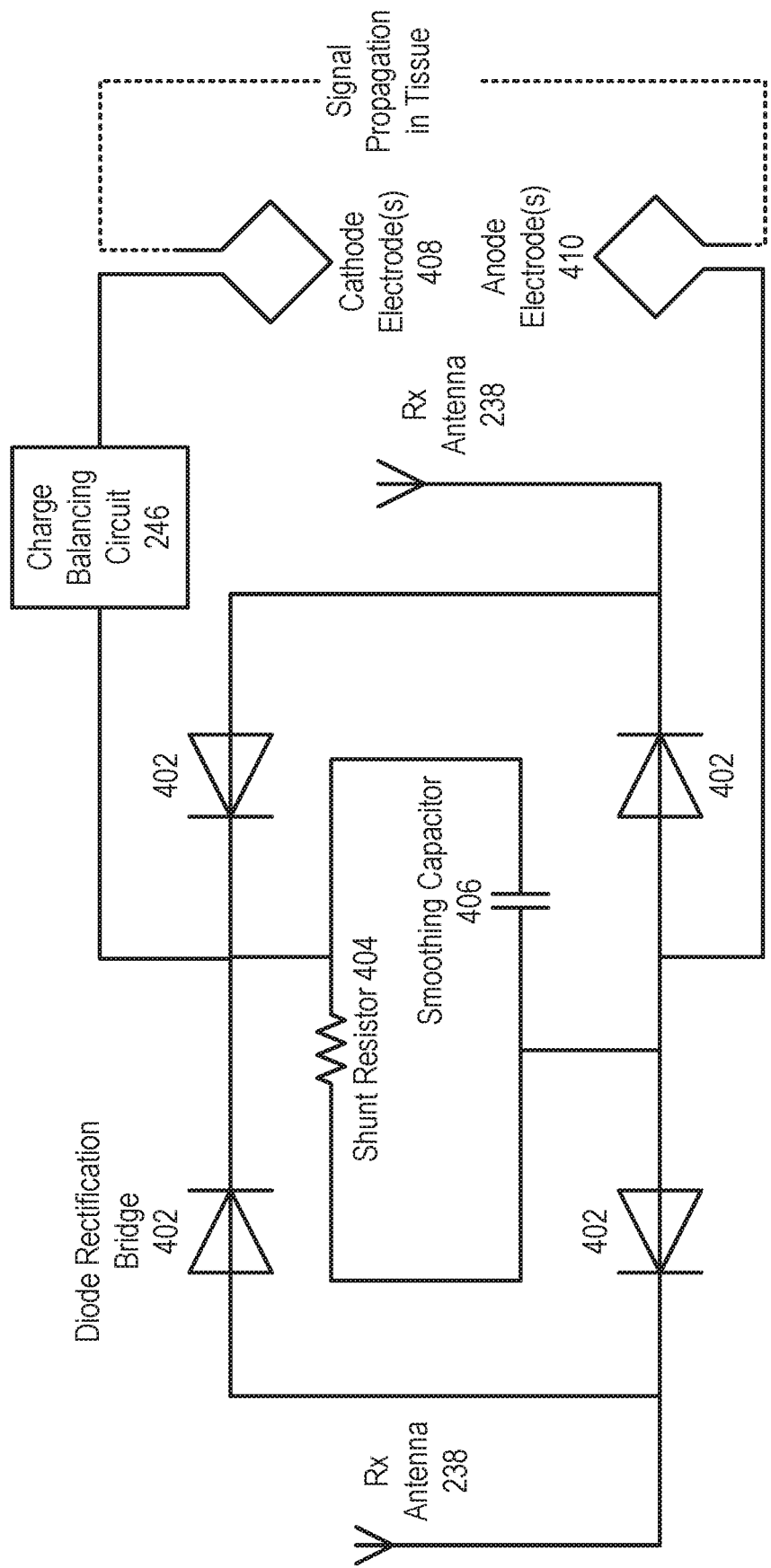
FIG. 4 is a circuit diagram showing an example of a wireless implantable stimulator device.

FIG. 4 is a circuit diagram showing an example of a wireless stimulator device 114. This example contains paired electrodes, comprising cathode electrode(s) 408 and anode electrode(s) 410, as shown. When energized, the charged electrodes create a volume conduction field of current density within the tissue. In this implementation, the wireless energy is received through a dipole antenna(s) 238. At least four diodes are connected together to form a full wave bridge rectifier 402 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may lead to a low threshold voltage. In this implementation, a zero biased diode rectifier results in a low output impedance for the device. A resistor 404 and a smoothing capacitor 406 are placed across the output nodes of the bridge rectifier to discharge the electrodes to the ground of the bridge anode. The rectification bridge 402 includes two branches of diode pairs connecting an anode-to-anode and then cathode to cathode. The electrodes 408 and 410 are connected to the output of the charge balancing circuit 246.

Figure 5:
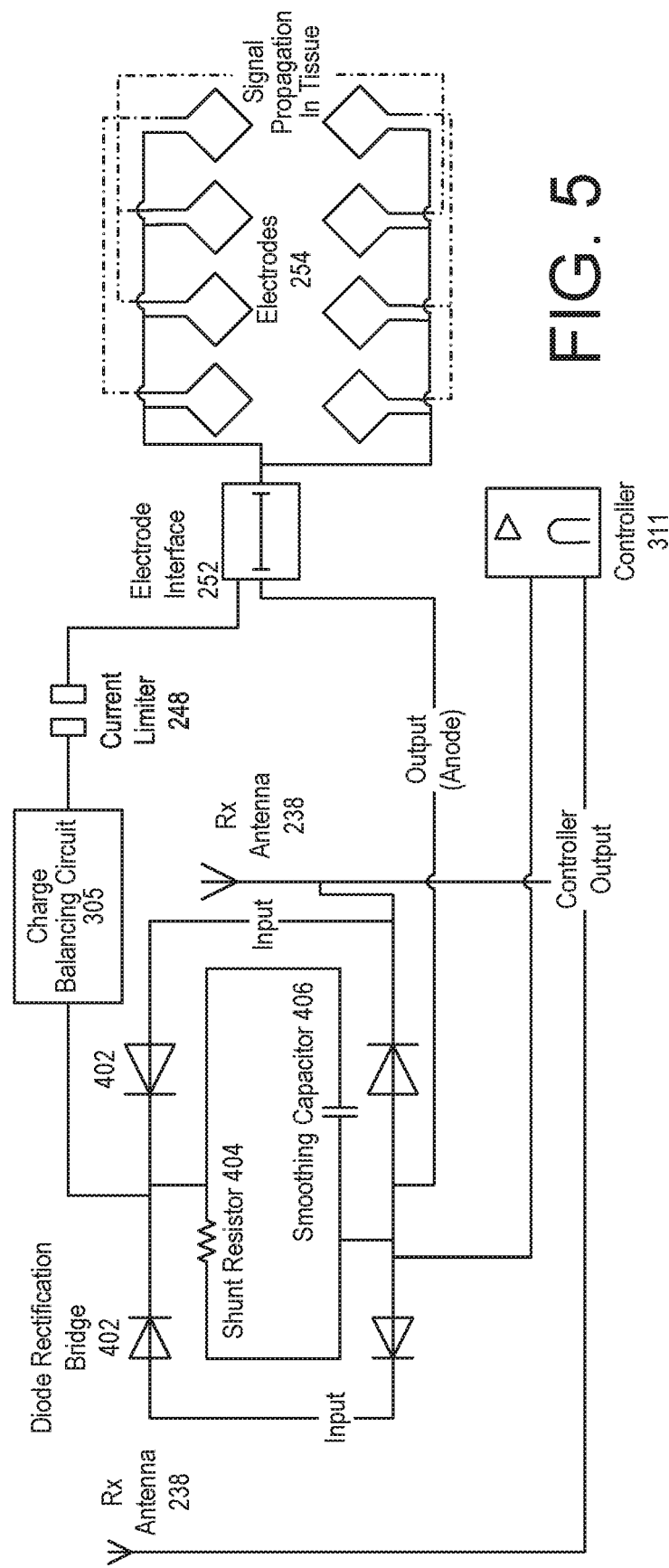
FIG. 5 is a circuit diagram of another example of a wireless implantable stimulator device.

FIG. 5 is a circuit diagram of another example of a wireless stimulator device 114. The example shown in FIG. 5 includes multiple electrode control and may employ full closed loop control. The wireless stimulation device includes an electrode array 254 in which the polarity of the electrodes can be assigned as cathodic or anodic, and for which the electrodes can be alternatively not powered with any energy. When energized, the charged electrodes create a volume conduction field of current density within the tissue. In this implementation, the wireless energy is received by the device through the dipole antenna(s) 238. The electrode array 254 is controlled through an on-board controller circuit 242 that sends the appropriate bit information to the electrode interface 252 in order to set the polarity of each electrode in the array, as well as power to each individual electrode. The lack of power to a specific electrode would set that electrode in a functional OFF position. In another implementation (not shown), the amount of current sent to each electrode is also controlled through the controller 242. The controller current, polarity and power state parameter data, shown as the controller output, is be sent back to the antenna(s) 238 for telemetry transmission back to the pulse generator module 106. The controller 242 also includes the functionality of current monitoring and sets a bit register counter so that the status of total current drawn can be sent back to the pulse generator module 106.

At least four diodes can be connected together to form a full wave bridge rectifier 302 attached to the dipole antenna(s) 238. Each diode, up to 100 micrometers in length, uses a junction potential to prevent the flow of negative electrical current, from cathode to anode, from passing through the device when said current does not exceed the reverse threshold. For neural stimulation via wireless power, transmitted through tissue, the natural inefficiency of the lossy material may lead to a low threshold voltage. In this implementation, a zero biased diode rectifier results in a low output impedance for the device. A resistor 404 and a smoothing capacitor 406 are placed across the output nodes of the bridge rectifier to discharge the electrodes to the ground of the bridge anode. The rectification bridge 402 may include two branches of diode pairs connecting an anode-to-anode and then cathode to cathode. The electrode polarity outputs, both cathode 408 and anode 410 are connected to the outputs formed by the bridge connection. Charge balancing circuitry 246 and current limiting circuitry 248 are placed in series with the outputs.

Figure 6:
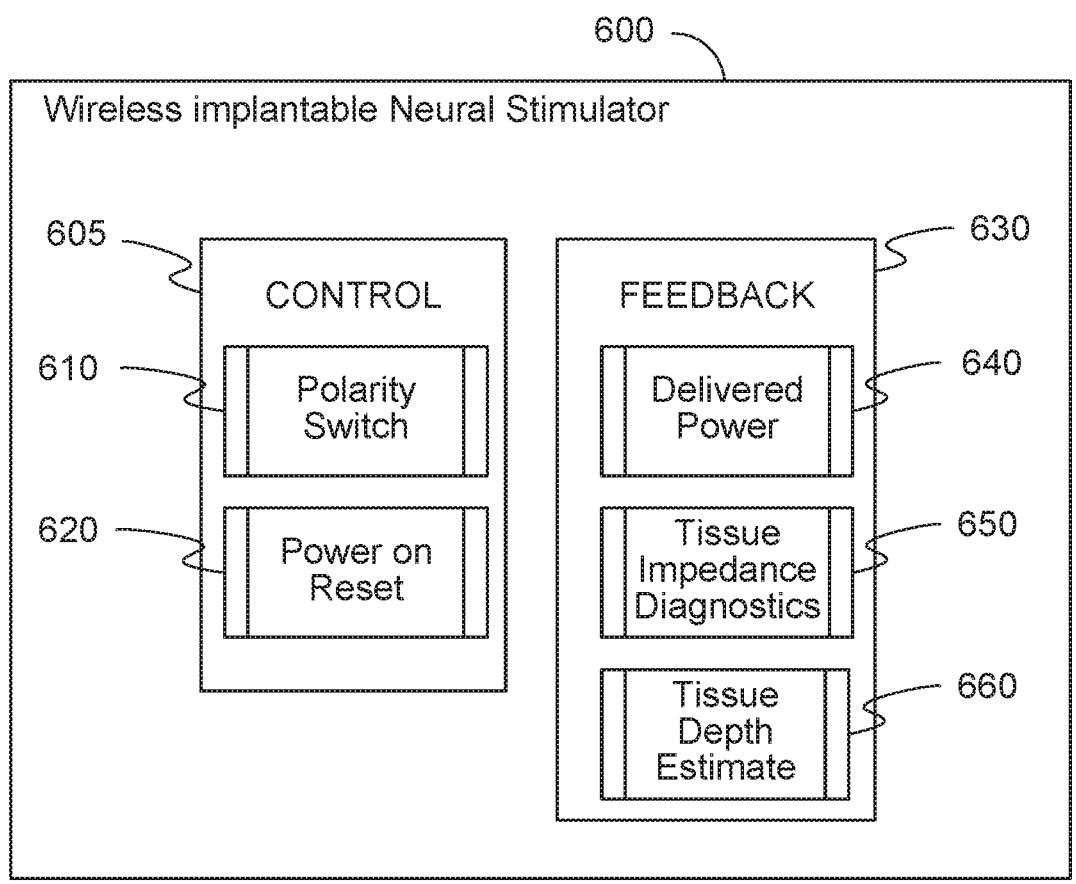
FIG. 6 is a block diagram showing an example of control and feedback functions of a wireless implantable stimulator device.

FIG. 6 is a block diagram showing an example of control functions 605 and feedback functions 630 of an implantable wireless stimulator device 600, such as the ones described above or further below. An example implementation may be a wireless stimulator device module 114, as discussed above in association with FIG. 2. Control functions 605 include functions 610 for polarity switching of the electrodes and functions 620 for power-on reset.

Polarity switching functions 610 may employ, for example, a polarity routing switch network to assign polarities to electrodes 254. The assignment of polarity to an electrode may, for instance, be one of: a cathode (negative polarity), an anode (positive polarity), or a neutral (off) polarity. The polarity assignment information for each of the electrodes 254 may be contained in the input signal received by implantable wireless stimulator device 600 through Rx antenna 238 from RF pulse generator module 106. Because a programmer module 102 may control RF pulse generator module 106, the polarity of electrodes 254 may be controlled remotely by a programmer through programmer module 102, as shown in FIG. 2.

Power-on reset functions 620 may reset the polarity assignment of each electrode immediately on each power-on event. As will be described in further detail below, this reset operation may cause RF pulse generator module 106 to transmit the polarity assignment information to the implantable wireless stimulator device 600. Once the polarity assignment information is received by the implantable wireless stimulator device 600, the polarity assignment information may be stored in a register file, or other short-term memory component. Thereafter the polarity assignment information may be used to configure the polarity assignment of each electrode. If the polarity assignment information transmitted in response to the reset encodes the same polarity state as before the power-on event, then the polarity state of each electrode can be maintained before and after each power-on event.

Feedback functions 630 include functions 640 for monitoring delivered power to electrodes 254 and functions 650 for making impedance diagnosis of electrodes 254. For example, delivered power functions 640 may provide data encoding the amount of power being delivered from electrodes 254 to the excitable tissue and tissue impedance diagnostic functions 650 may provide data encoding the diagnostic information of tissue impedance. The tissue impedance is the electrical impedance of the tissue as seen between negative and positive electrodes when a stimulation current is being released between negative and positive electrodes.

Feedback functions 630 may additionally include tissue depth estimate functions 660 to provide data indicating the overall tissue depth that the input radio frequency (RF) signal from the pulse generator module, such as, for example, RF pulse generator module 106, has penetrated before reaching the implanted antenna, such as, for example, RX antenna 238, within the wireless implantable stimulator device 600, such as, for example, implanted wireless stimulator device 114. For instance, the tissue depth estimate may be provided by comparing the power of the received input signal to the power of the RF pulse transmitted by the RF pulse generator 106. The ratio of the power of the received input signal to the power of the RF pulse transmitted by the RF pulse generator 106 may indicate an attenuation caused by wave propagation through the tissue. For example, the second harmonic described below may be received by the RF pulse generator 106 and used with the power of the input signal sent by the RF pulse generator to determine the tissue depth. The attenuation may be used to infer the overall depth of implantable wireless stimulator device 600 underneath the skin.

The data from blocks 640, 650, and 660 may be transmitted, for example, through Tx antenna 110 to an implantable RF pulse generator 106, as illustrated in FIGS. 1 and 2.

As discussed above in association with FIGS. 1, 2, 4, and 5, an implantable wireless stimulator device 600 may utilize rectification circuitry to convert the input signal (e.g., having a carrier frequency within a range from about 300 MHz to about 8 GHz) to a direct current (DC) power to drive the electrodes 254. Some implementations may provide the capability to regulate the DC power remotely. Some implementations may further provide different amounts of power to different electrodes, as discussed in further detail below.

Figure 7:
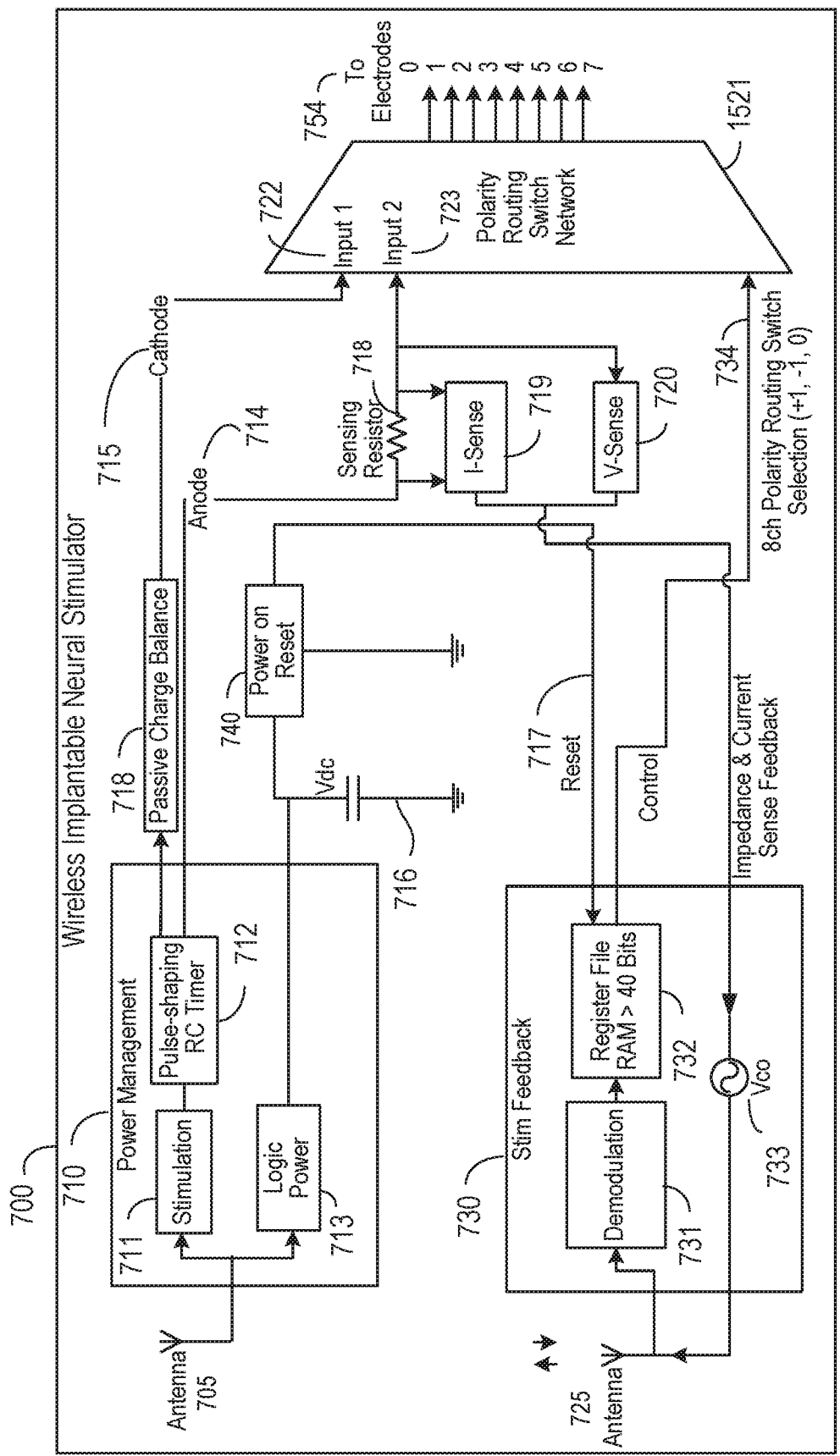
FIG. 7 is a schematic showing an example of a wireless implantable stimulator device with components to implement control and feedback functions.

FIG. 7 is a schematic showing an example of an implantable wireless stimulator device 700 with components to implement control and feedback functions as discussed above in association with FIG. 6. An RX antenna 705 receives the input signal. The RX antenna 705 may be embedded as a dipole, microstrip, folded dipole or other antenna configuration other than a coiled configuration, as described above. The input signal has a carrier frequency in the GHz range and contains electrical energy for powering the wireless implantable stimulator device 700 and for providing stimulation pulses to electrodes 254. Once received by the antenna 705, the input signal is routed to power management circuitry 710. Power management circuitry 710 is configured to rectify the input signal and convert it to a DC power source. For example, the power management circuitry 710 may include a diode rectification bridge such as the diode rectification bridge 402 illustrated in FIG. 4. The DC power source provides power to stimulation circuitry 711 and logic power circuitry 713. The rectification may utilize one or more full wave diode bridge rectifiers within the power management circuitry 710. In one implementation, a resistor can be placed across the output nodes of the bridge rectifier to discharge the electrodes to the ground of the bridge anode, as illustrated by the shunt register 404 in FIG. 7.

Figure 8:
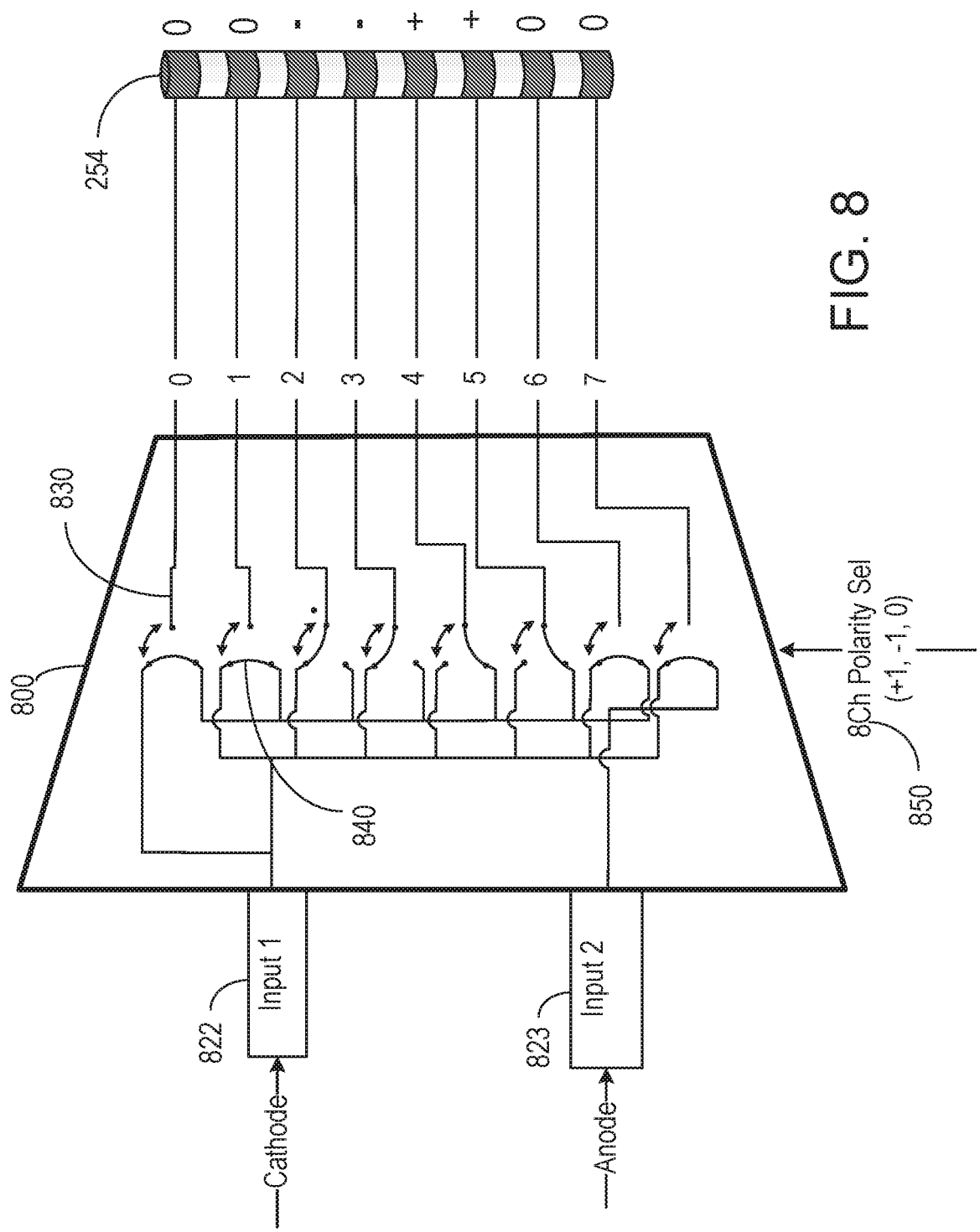
FIG. 8 is a schematic of an example of a polarity routing switch network.

Turning momentarily to FIG. 8, a schematic of an example of a polarity routing switch network 800 is shown. As discussed above, the cathodic (−) energy and the anodic energy are received at input 1 (block 722) and input 2 (block 723), respectively. Polarity routing switch network 800 has one of its outputs coupled to an electrode of electrodes 254 which can include as few as two electrodes, or as many as sixteen electrodes. Eight electrodes are shown in this implementation as an example.

Polarity routing switch network 800 is configured to either individually connect each output to one of input 1 or input 2, or disconnect the output from either of the inputs. This selects the polarity for each individual electrode of electrodes 254 as one of: neutral (off), cathode (negative), or anode (positive). Each output is coupled to a corresponding three-state switch 830 for setting the connection state of the output. Each three-state switch is controlled by one or more of the bits from the selection input 850. In some implementations, selection input 850 may allocate more than one bits to each three-state switch. For example, two bits may encode the three-state information. Thus, the state of each output of polarity routing switch device 800 can be controlled by information encoding the bits stored in the register 732, which may be set by polarity assignment information received from the remote RF pulse generator module 106, as described further below.

Returning to FIG. 7, power and impedance sensing circuitry may be used to determine the power delivered to the tissue and the impedance of the tissue. For example, a sensing resistor 718 may be placed in serial connection with the anodic branch 714. Current sensing circuit 719 senses the current across the resistor 718 and voltage sensing circuit 720 senses the voltage across the resistor. The measured current and voltage may correspond to the actual current and voltage applied by the electrodes to the tissue.

As described below, the measured current and voltage may be provided as feedback information to RF pulse generator module 106. The power delivered to the tissue may be determined by integrating the product of the measured current and voltage over the duration of the waveform being delivered to electrodes 254. Similarly, the impedance of the tissue may be determined based on the measured voltage being applied to the electrodes and the current being applied to the tissue. Alternative circuitry (not shown) may also be used in lieu of the sensing resistor 718, depending on implementation of the feature and whether both impedance and power feedback are measured individually, or combined.

The measurements from the current sensing circuitry 719 and the voltage sensing circuitry 720 may be routed to a voltage controlled oscillator (VCO) 733 or equivalent circuitry capable of converting from an analog signal source to a carrier signal for modulation. VCO 733 can generate a digital signal with a carrier frequency. The carrier frequency may vary based on analog measurements such as, for example, a voltage, a differential of a voltage and a power, etc. VCO 733 may also use amplitude modulation or phase shift keying to modulate the feedback information at the carrier frequency. The VCO or the equivalent circuit may be generally referred to as an analog controlled carrier modulator. The modulator may transmit information encoding the sensed current or voltage back to RF pulse generator 106.

Antenna 725 may transmit the modulated signal, for example, in the GHz frequency range, back to the RF pulse generator module 106. In some embodiments, antennas 705 and 725 may be the same physical antenna. In other embodiments, antennas 705 and 725 may be separate physical antennas. In the embodiments of separate antennas, antenna 725 may operate at a resonance frequency that is higher than the resonance frequency of antenna 705 to send stimulation feedback to RF pulse generator module 106. In some embodiments, antenna 725 may also operate at the higher resonance frequency to receive data encoding the polarity assignment information from RF pulse generator module 106.

Antenna 725 may include a telemetry antenna 725 which may route received data, such as polarity assignment information, to the stimulation feedback circuit 730. The encoded polarity assignment information may be on a band in the GHz range. The received data may be demodulated by demodulation circuitry 731 and then stored in the register file 732. The register file 732 may be a volatile memory. Register file 732 may be an 8-channel memory bank that can store, for example, several bits of data for each channel to be assigned a polarity. Some embodiments may have no register file, while some embodiments may have a register file up to 64 bits in size. The information encoded by these bits may be sent as the polarity selection signal to polarity routing switch network 721, as indicated by arrow 734. The bits may encode the polarity assignment for each output of the polarity routing switch network as one of: + (positive), − (negative), or 0 (neutral). Each output connects to one electrode and the channel setting determines whether the electrode will be set as an anode (positive), cathode (negative), or off (neutral).

Returning to power management circuitry 710, in some embodiments, approximately 90% of the energy received is routed to the stimulation circuitry 711 and less than 10% of the energy received is routed to the logic power circuitry 713. Logic power circuitry 713 may power the control components for polarity and telemetry. In some implementations, the power circuitry 713, however, does not provide the actual power to the electrodes for stimulating the tissues. In certain embodiments, the energy leaving the logic power circuitry 713 is sent to a capacitor circuit 716 to store a certain amount of readily available energy. The voltage of the stored charge in the capacitor circuit 716 may be denoted as Vdc. Subsequently, this stored energy is used to power a power-on reset circuit 716 configured to send a reset signal on a power-on event. If the wireless implantable neural stimulator 700 loses power for a certain period of time, for example, in the range from about 1 millisecond to over 10 milliseconds, the contents in the register file 732 and polarity setting on polarity routing switch network 721 may be zeroed. The implantable wireless stimulation device 700 may lose power, for example, when it becomes less aligned with RF pulse generator module 106. Using this stored energy, power-on reset circuit 740 may provide a reset signal as indicated by arrow 717. This reset signal may cause stimulation feedback circuit 730 to notify RF pulse generator module 106 of the loss of power. For example, stimulation feedback circuit 730 may transmit a telemetry feedback signal to RF pulse generator module 106 as a status notification of the power outage. This telemetry feedback signal may be transmitted in response to the reset signal and immediately after power is back on wireless stimulation device 700. RF pulse generator module 106 may then transmit one or more telemetry packets to implantable wireless stimulation device. The telemetry packets contain polarity assignment information, which may be saved to register file 732 and may be sent to polarity routing switch network 721. Thus, polarity assignment information in register file 732 may be recovered from telemetry packets transmitted by RF pulse generator module 106 and the polarity assignment for each output of polarity routing switch network 721 may be updated accordingly based on the polarity assignment information.

The telemetry antenna 725 may transmit the telemetry feedback signal back to RF pulse generator module 106 at a frequency higher than the characteristic frequency of an RX antenna 705. In one implementation, the telemetry antenna 725 can have a heightened resonance frequency that is the second harmonic of the characteristic frequency of RX antenna 705. For example, the second harmonic may be utilized to transmit power feedback information regarding an estimate of the amount of power being received by the electrodes. The feedback information may then be used by the RF pulse generator in determining any adjustment of the power level to be transmitted by the RF pulse generator 106. In a similar manner, the second harmonic energy can be used to detect the tissue depth. The second harmonic transmission can be detected by an external antenna, for example, on RF pulse generator module 106 that is tuned to the second harmonic. As a general matter, power management circuitry 710 may contain rectifying circuits that are non-linear device capable of generating harmonic energies from input signal. Harvesting such harmonic energy for transmitting telemetry feedback signal could improve the efficiency of implantable wireless stimulator device 700.

Figure 9A:
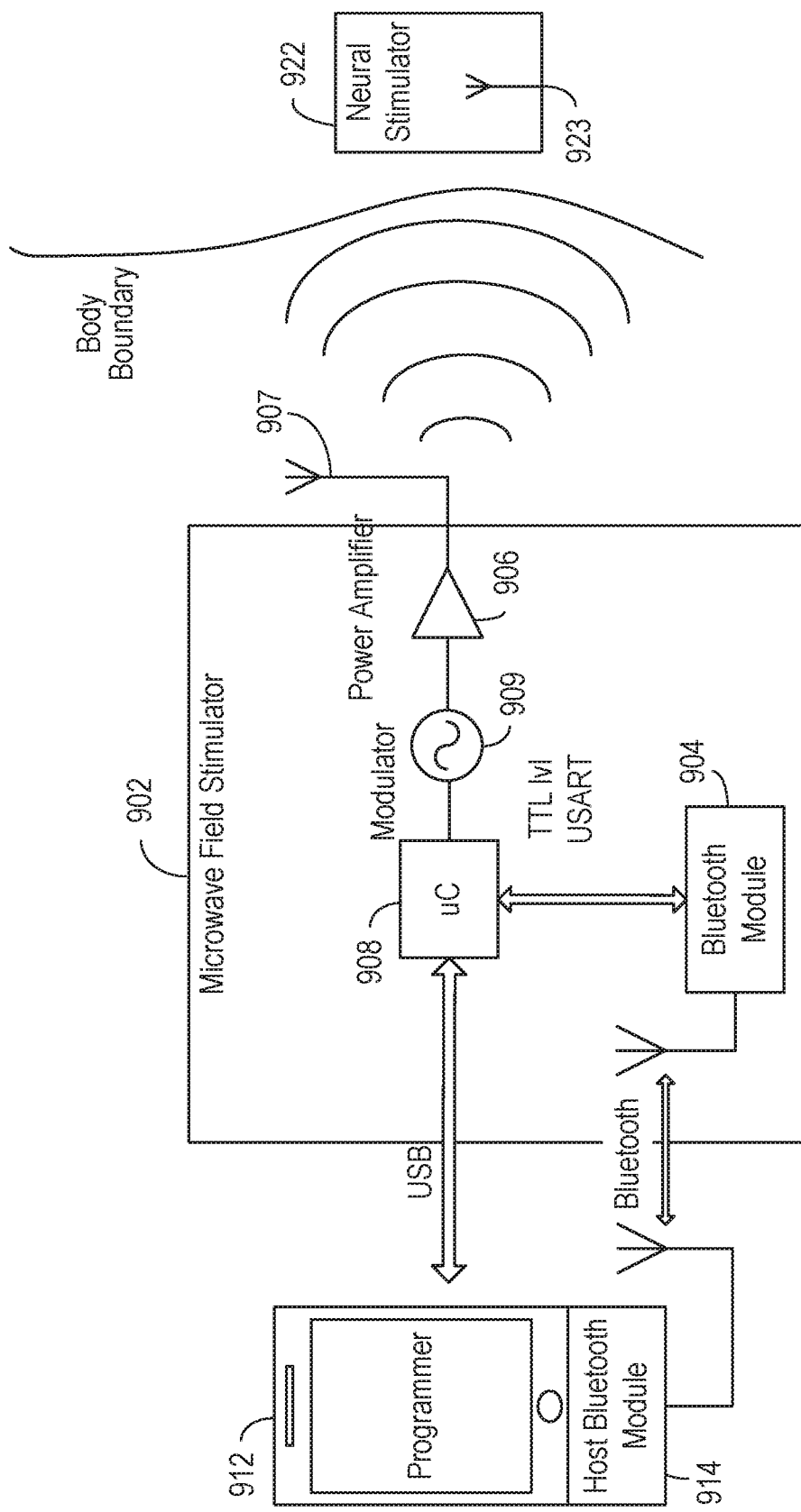
FIG. 9A is a diagram of an example microwave field stimulator (MFS) operating along with a wireless implantable stimulator device.

FIG. 9A is a diagram of an example implementation of a microwave field stimulator (MFS) 902 as part of a stimulation system utilizing an implantable wireless stimulator device 922. In this example, the MFS 902 is external to a patient's body and may be placed within in close proximity, for example, within 3 feet, to an implantable wireless stimulator device 922. The RF pulse generator module 106 may be one example implementation of MFS 902. MFS 902 may be generally known as a controller module. The implantable wireless stimulator device 922 is a passive device. The implantable wireless stimulator device 922 does not have its own independent power source, rather it receives power for its operation from transmission signals emitted from a TX antenna powered by the MFS 902, as discussed above.

In certain embodiments, the MFS 902 may communicate with a programmer 912. The programmer 912 may be a mobile computing device, such as, for example, a laptop, a smart phone, a tablet, etc. The communication may be wired, using for example, a USB or firewire cable. The communication may also be wireless, utilizing for example, a bluetooth protocol implemented by a transmitting blue tooth module 904, which communicates with the host bluetooth module 914 within the programmer 912.

The MFS 902 may additionally communicate with wireless stimulator device 922 by transmitting a transmission signal through a Tx antenna 907 coupled to an amplifier 906. The transmission signal may propagate through skin and underlying tissues to arrive at the Rx antenna 923 of the wireless stimulator device 922. In some implementations, the wireless stimulator device 922 may transmit a telemetry feedback signal back to microwave field stimulator 902.

The microwave field stimulator 902 may include a microcontroller 908 configured to manage the communication with a programmer 912 and generate an output signal. The output signal may be used by the modulator 909 to modulate a RF carrier signal. The frequency of the carrier signal may be in the microwave range, for example, from about 300 MHz to about 8 GHz, preferably from about 800 MHz to 1.3 GHz. The modulated RF carrier signal may be amplified by an amplifier 906 to provide the transmission signal for transmission to the wireless stimulator device 922 through a TX antenna 907.

Figure 9B:
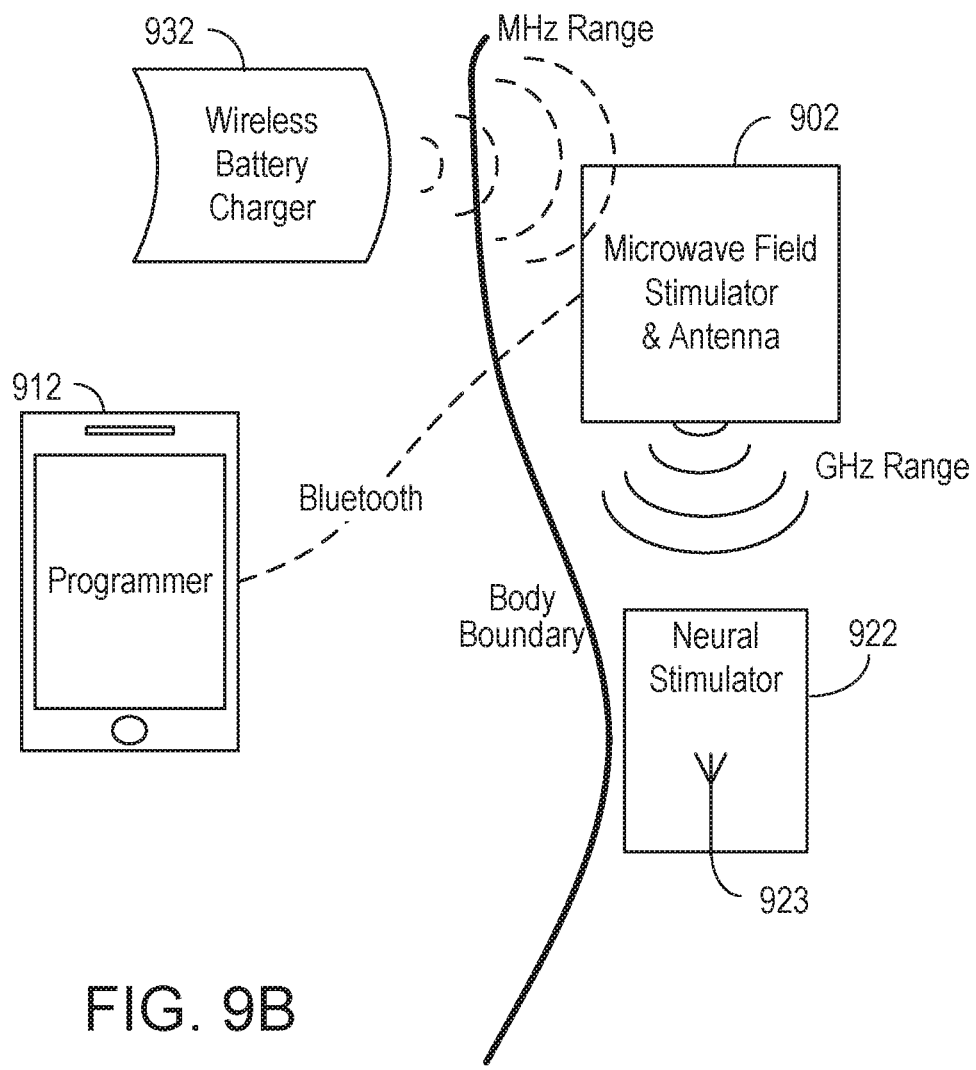
FIG. 9B is a diagram of another example MFS operating along with a wireless implantable stimulator device.

FIG. 9B is a diagram of another example of an implementation of a microwave field stimulator 902 as part of a stimulation system utilizing a wireless stimulator device 922. In this example, the microwave field stimulator 902 may be embedded in the body of the patient, for example, subcutaneously. The embedded microwave field stimulator 902 may receive power from a detached, remote wireless battery charger 932.

The power from the wireless battery charger 932 to the embedded microwave field stimulator 902 may be transmitted at a frequency in the MHz or GHz range. The microwave field stimulator 902 shall be embedded subcutaneously at a very shallow depth (e.g., less than 1 cm), and alternative coupling methods may be used to transfer energy from wireless battery charger 932 to the embedded MFS 902 in the most efficient manner as is well known in the art.

In some embodiments, the microwave field stimulator 902 may be adapted for placement at the epidural layer of a spinal column, near or on the dura of the spinal column, in tissue in close proximity to the spinal column, in tissue located near a dorsal horn, in dorsal root ganglia, in one or more of the dorsal roots, in dorsal column fibers, or in peripheral nerve bundles leaving the dorsal column of the spine.

In this embodiment, the microwave field stimulator 902 shall transmit power and parameter signals to a passive Tx antenna also embedded subcutaneously, which shall be coupled to the RX antenna within the wireless stimulator device 922. The power required in this embodiment is substantially lower since the TX antenna and the RX antenna are already in body tissue and there is no requirement to transmit the signal through the skin.

Figure 10:
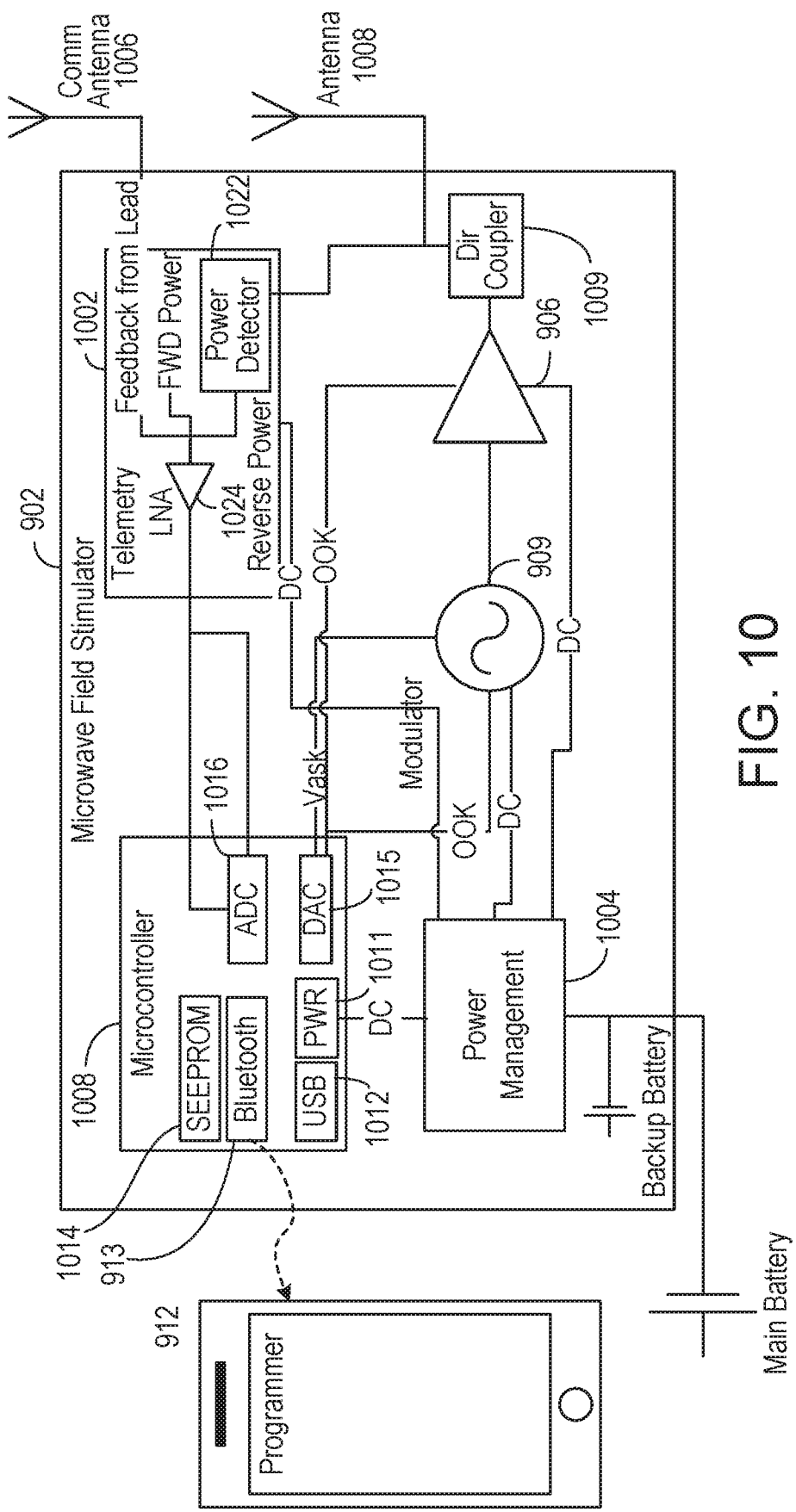
FIG. 10 is a detailed diagram of an example MFS.

FIG. 10 is a detailed diagram of an example microwave field stimulator 902. A microwave field stimulator 902 may include a microcontroller 908, a telemetry feedback module 1002, and a power management module 1004. The microwave field stimulator 902 has a two-way communication schema with a programmer 912, as well as with a communication or telemetry antenna 1006. The microwave field stimulator 902 sends output power and data signals through a TX antenna 1008.

The microcontroller 908 may include a storage device 1014, a bluetooth interface 1013, a USB interface 1012, a power interface 1011, an analog-to-digital converter (ADC) 1016, and a digital to analog converter (DAC) 1015. Implementations of a storage device 1014 may include non-volatile memory, such as, for example, static electrically erasable programmable read-only memory (SEEPROM) or NAND flash memory. A storage device 1014 may store waveform parameter information for the microcontroller 908 to synthesize the output signal used by modulator 909. The stimulation waveform may include multiple pulses. The waveform parameter information may include the shape, duration, amplitude of each pulse, as well as pulse repetition frequency. A storage device 1014 may additionally store polarity assignment information for each electrode of the wireless stimulator device 922. The Bluetooth interface 1013 and USB interface 1012 respectively interact with either the bluetooth module 1004 or the USB module to communicate with the programmer 912.

The communication antenna 1006 and a TX antenna 1008 may, for example, be configured in a variety of sizes and form factors, including, but not limited to a patch antenna, a slot antenna, or a dipole antenna. The TX antenna 1008 may be adapted to transmit a transmission signal, in addition to power, to the implantable, passive neural stimulator device 922. As discussed above, an output signal generated by the microcontroller 908 may be used by the modulator 909 to provide the instructions for creation of a modulated RF carrier signal. The RF carrier signal may be amplified by amplifier 906 to generate the transmission signal. A directional coupler 1009 may be utilized to provide two-way coupling so that both the forward power of the transmission signal flow transmitted by the TX antenna 1008 and the reverse power of the reflected transmission may be picked up by power detector 1022 of telemetry feedback module 1002. In some implementations, a separate communication antenna 1006 may function as the receive antenna for receiving telemetry feedback signal from the wireless stimulator device 922. In some configurations, the communication antenna may operate at a higher frequency band than the TX antenna 1008. For example, the communication antenna 1006 may have a characteristic frequency that is a second harmonic of the characteristic frequency of TX antenna 1008, as discussed above.

In some embodiments, the microwave field stimulator 902 may additionally include a telemetry feedback module 902. In some implementations, the telemetry feedback module 1002 may be coupled directly to communication antenna 1006 to receive telemetry feedback signals. The power detector 1022 may provide a reading of both the forward power of the transmission signal and a reverse power of a portion of the transmission signal that is reflected during transmission. The telemetry signal, forward power reading, and reverse power reading may be amplified by low noise amplifier (LNA) 1024 for further processing. For example, the telemetry module 902 may be configured to process the telemetry feedback signal by demodulating the telemetry feedback signal to extract the encoded information. Such encoded information may include, for example, a status of the wireless stimulator device 922 and one or more electrical parameters associated with a particular channel (electrode) of the wireless stimulator device 922. Based on the decoded information, the telemetry feedback module 1002 may be used to calculate a desired operational characteristic for the wireless stimulator device 922.

Some embodiments of the MFS 902 may further include a power management module 1004. A power management module 1004 may manage various power sources for the MFS 902. Example power sources include, but are not limited to, lithium-ion or lithium polymer batteries. The power management module 1004 may provide several operational modes to save battery power. Example operation modes may include, but are not limited to, a regular mode, a low power mode, a sleep mode, a deep sleep/hibernate mode, and an off mode. The regular mode provides regulation of the transmission of transmission signals and stimulus to the wireless stimulator device 922. In regular mode, the telemetry feedback signal is received and processed to monitor the stimuli as normal. Low-power mode also provides regulation of the transmission of transmission signals and stimulus to the electrodes of the wireless stimulation device. However, under this mode, the telemetry feedback signal may be ignored. More specifically, the telemetry feedback signal encoding the stimulus power may be ignored, thereby saving MFS 902 overall power consumption. Under sleep mode, the transceiver and amplifier 906 are turned off, while the microcontroller is kept on with the last saved state in its memory. Under the deep sleep/hibernate mode, the transceiver and amplifier 906 are turned off, while the microcontroller is in power down mode, but power regulators are on. Under the off mode, all transceiver, microcontroller and regulators are turned off achieving zero quiescent power.

Figure 11:
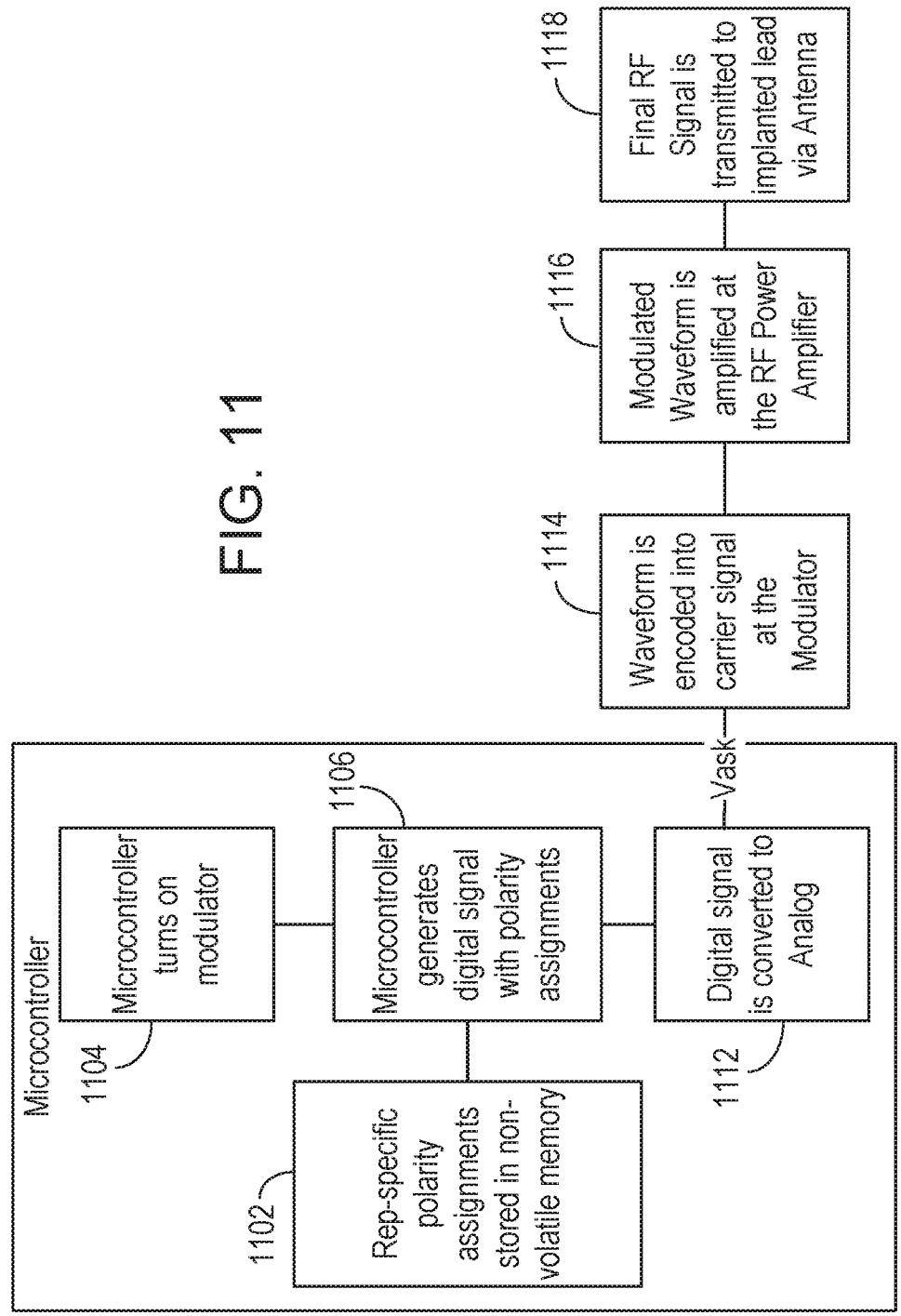
FIG. 11 is a flowchart showing an example process in which the MFS transmits polarity setting information to the wireless implantable stimulator device.

FIG. 11 is a flowchart showing an example process in which the microwave field stimulator 902 transmits polarity setting information to the wireless stimulator device 922. Polarity assignment information is stored in a non-volatile memory 1102 within the microcontroller 908 of the MFS 902. The polarity assignment information may be representative-specific and may be chosen to meet the specific need of a particular patient. Based on the polarity assignment information chosen for a particular patient, the microcontroller 908 executes a specific routine for assigning polarity to each electrode of the electrode array. The particular patient has an wireless stimulation device as described above.

In some implementations, the polarity assignment procedure includes sending a signal to the wireless stimulation device with an initial power-on portion followed by a configuration portion that encodes the polarity assignments. The power-on portion may, for example, simply include the RF carrier signal. The initial power-on portion has a duration that is sufficient to power-on the wireless stimulation device and allow the device to reset into a configuration mode. Once in the configuration mode, the device reads the encoded information in the configuration portion and sets the polarity of the electrodes as indicated by the encoded information.

Thus, in some implementations, the microcontroller 908 turns on the modulator 909 so that the unmodulated RF carrier is sent to the wireless stimulator device 1104. After a set duration, the microcontroller 908 automatically initiates transmitting information encoding the polarity assignment. In this scenario, the microcontroller 908 transmits the polarity settings in the absence of handshake signals from the wireless stimulation device. Because the microwave field stimulator 902 is operating in close proximity to wireless stimulator device 922, signal degradation may not be severe enough to warrant the use of handshake signals to improve quality of communication.

To transmit the polarity information, the microcontroller 908 reads the polarity assignment information from the non-volatile memory and generates a digital signal encoding the polarity information 1106. The digital signal encoding the polarity information may be converted to an analog signal, for example, by a digital-to-analog (DAC) converter 1112. The analog signal encoding the waveform may modulate a carrier signal at modulator 909 to generate a configuration portion of the transmission signal (1114). This configuration portion of the transmission signal may be amplified by the power amplifier 906 to generate the signal to be transmitted by antenna 907 (1116). Thereafter, the configuration portion of the transmission signal is transmitted to the wireless stimulator device 922 (1118).

Once the configuration portion is transmitted to the wireless stimulation device, the microcontroller 908 initiates the stimulation portion of the transmission signal. Similar to the configuration portion, the microcontroller 908 generates a digital signal that encodes the stimulation waveform. The digital signal is converted to an analog signal using the DAC. The analog signal is then used to modulate a carrier signal at modulator 909 to generate a stimulation portion of the transmission signal.

In other implementations, the microcontroller 908 initiates the polarity assignment protocol after the microcontroller 908 has recognized a power-on reset signal transmitted by the neural stimulator. The power-on reset signal may be extracted from a feedback signal received by microcontroller 908 from the wireless stimulator device 922. The feedback signal may also be known as a handshake signal in that it alerts the microwave field stimulator 902 of the ready status of the wireless stimulator device 922. In an example, the feedback signal may be demodulated and sampled to digital domain before the power-on reset signal is extracted in the digital domain.

Figure 12:
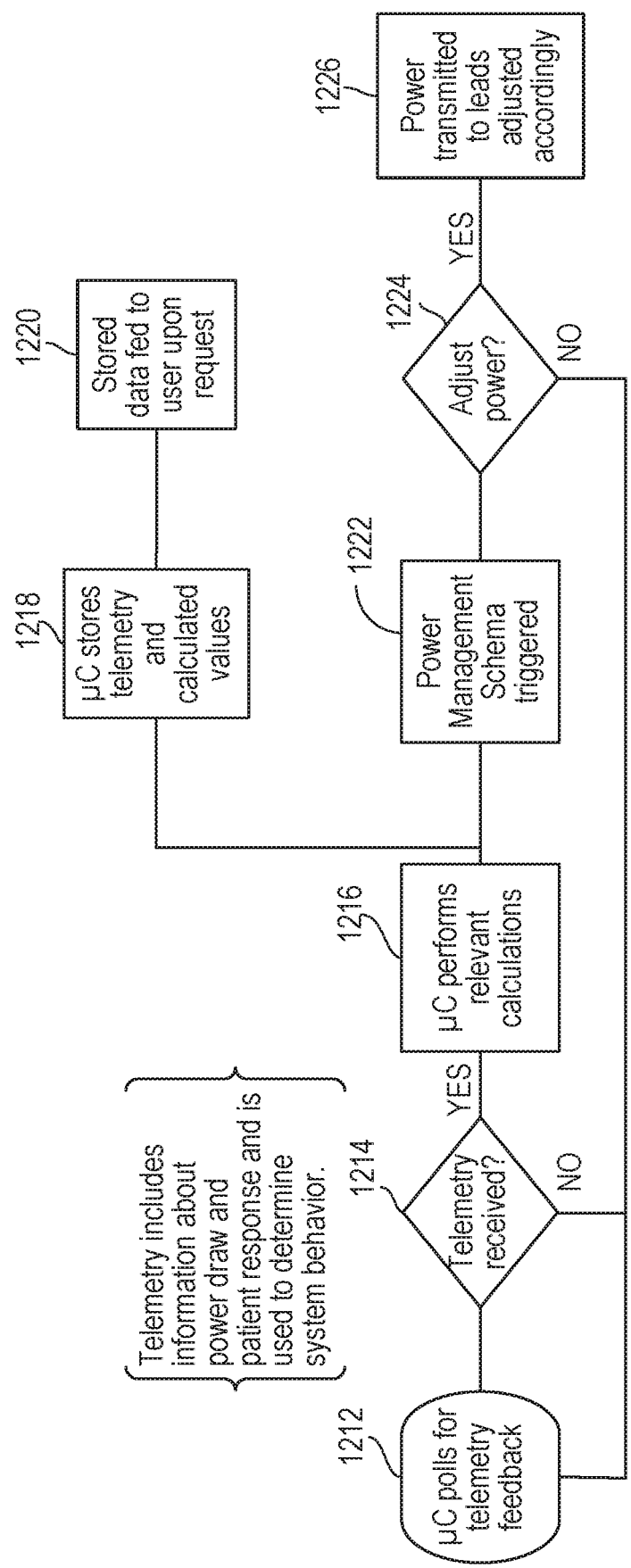
FIG. 12 is another flow chart showing an example process in which the MFS receives and processes the telemetry feedback signal to make adjustments to subsequent transmissions.

FIG. 12 is a flow chart showing an example of the process in which the microwave field stimulator 902 receives and processes the telemetry feedback signal to make adjustments to subsequent transmissions.

In some implementations, the microcontroller 908 polls the telemetry feedback module 1002 (1212). The polling is to determine whether a telemetry feedback signal has been received (1214). The telemetry feedback signal may include information based on which the MFS 902 may ascertain the power consumption being utilized by the electrodes of the wireless stimulator device 922. This information may also be used to determine the operational characteristics of the combination system of the MFS 902 and the wireless stimulator device 922, as will be discussed in further detail in association with FIG. 13. The information may also be logged by the microwave field stimulator 902 so that the response of the patient may be correlated with past treatments received over time. The correlation may reveal the patient's individual response to the treatments the patient has received up to date.

If the microcontroller 908 determines that telemetry feedback module 1002 has not yet received telemetry feedback signal, microcontroller 908 may continue polling (1212). If the microcontroller 908 determines that telemetry feedback module 1002 has received telemetry feedback signal, the microcontroller 908 may extract the information contained in the telemetry feedback signal to perform calculations (1216). The extraction may be performed by demodulating the telemetry feedback signal and sampling the demodulated signal in the digital domain. The calculations may reveal operational characteristics of the wireless stimulator device 922, including, for example, voltage or current levels associated with a particular electrode, power consumption of a particular electrode, and/or impedance of the tissue being stimulated through the electrodes.

Thereafter, in certain embodiments, the microcontroller 908 may store information extracted from the telemetry signals as well as the calculation results (1218). The stored data may be provided to a user through the programmer upon request (1220). The user may be the patient, the doctor, or representatives from the manufacturer. The data may be stored in a non-volatile memory, such as, for example, NAND flash memory or EEPROM.

In other embodiments, a power management schema may be triggered 1222 by the microcontroller (908). Under the power management schema, the microcontroller 908 may determine whether to adjust a parameter of subsequent transmissions (1224). The parameter may be amplitude or the stimulation waveform shape. In one implementation, the amplitude level may be adjusted based on a lookup table showing a relationship between the amplitude level and a corresponding power applied to the tissue through the electrodes. In one implementation, the waveform shape may be pre-distorted to compensate for a frequency response of the microwave field stimulator 902 and the wireless stimulator device 922. The parameter may also be the carrier frequency of the transmission signal. For example, the carrier frequency of the transmission signal may be modified to provide fine-tuning that improves transmission efficiency.

If an adjustment is made, the subsequently transmitted transmission signals are adjusted accordingly. If no adjustment is made, the microcontroller 908 may proceed back to polling the telemetry feedback module 1002 for telemetry feedback signal (1212).

In other implementations, instead of polling the telemetry feedback module 1002, the microcontroller 908 may wait for an interrupt request from telemetry feedback module 1002. The interrupt may be a software interrupt, for example, through an exception handler of the application program. The interrupt may also be a hardware interrupt, for example, a hardware event and handled by an exception handler of the underlying operating system.

Figure 13:
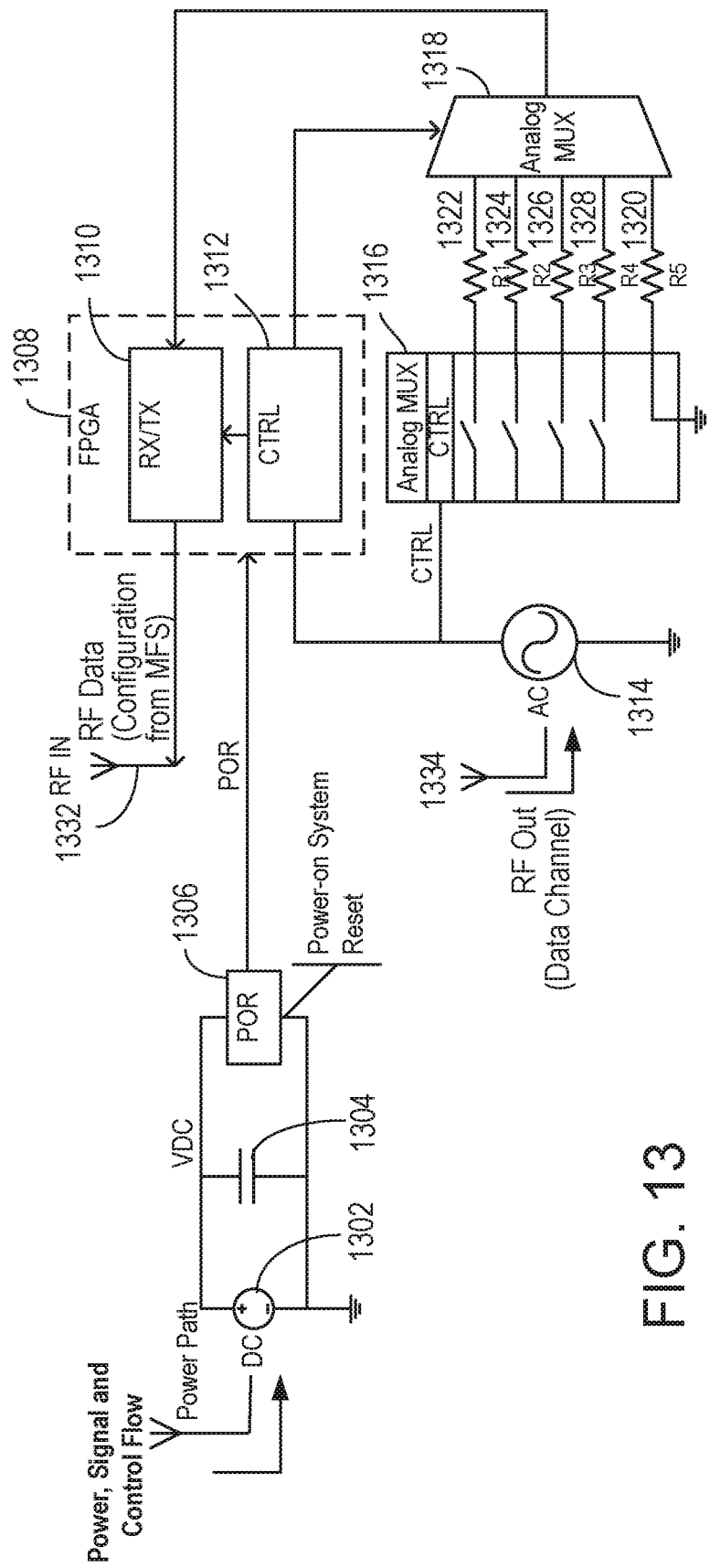
FIG. 13 is a schematic of an example implementation of power, signal and control flow on the wireless implantable stimulator device.

FIG. 13 is a schematic of an example implementation of the power, signal and control flow for the wireless stimulator device 922. A DC source 1302 obtains energy from the transmission signal received at the wireless stimulator device 922 during the initial power-on portion of the transmission signal while the RF power is ramping up. In one implementation, a rectifier may rectify the received power-on portion to generate the DC source 1302 and a capacitor 1304 may store a charge from the rectified signal during the initial portion. When the stored charge reaches a certain voltage (for example, one sufficient or close to sufficient to power operations of the wireless stimulator device 922), the power-on reset circuit 1306 may be triggered to send a power-on reset signal to reset components of the neural stimulator. The power-on set signal may be sent to circuit 1308 to reset, for example, digital registers, digital switches, digital logic, or other digital components, such as transmit and receive logic 1310. The digital components may also be associated with a control module 1312. For example, a control module 1312 may include electrode control 252, register file 732, etc. The power-on reset may reset the digital logic so that the circuit 1308 begins operating from a known, initial state.

In some implementations, the power-on reset signal may subsequently cause the FPGA circuit 1308 to transmit a power-on reset telemetry signal back to MFS 902 to indicate that the implantable wireless stimulator device 922 is ready to receive the configuration portion of the transmission signal that contains the polarity assignment information. For example, the control module 1312 may signal the RX/TX module 1310 to send the power-on reset telemetry signal to the telemetry antenna 1332 for transmission to MFS 902.

In other implementations, the power-on reset telemetry signal may not be provided. As discussed above, due to the proximity between MFS 902 and implantable, passive stimulator device 922, signal degradation due to propagation loss may not be severe enough to warrant implementations of handshake signals from the implantable, passive stimulator device 922 in response to the transmission signal. In addition, the operational efficiency of implantable, passive neural stimulator device 922 may be another factor that weighs against implementing handshake signals.

Once the FPGA circuit 1308 has been reset to an initial state, the FPGA circuit 1308 transitions to a configuration mode configured to read polarity assignments encoded on the received transmission signal during the configuration state. In some implementations, the configuration portion of the transmission signal may arrive at the wireless stimulation device through the RX antenna 1334. The transmission signal received may provide an AC source 1314. The AC source 1314 may be at the carrier frequency of the transmission signal, for example, from about 300 MHz to about 8 GHz.

Thereafter, the control module 1312 may read the polarity assignment information and set the polarity for each electrode through the analog mux control 1316 according to the polarity assignment information in the configuration portion of the received transmission signal. The electrode interface 252 may be one example of analog mux control 1316, which may provide a channel to a respective electrode of the implantable wireless stimulator device 922.

Once the polarity for each electrode is set through the analog mux control 1316, the implantable wireless stimulator device 922 is ready to receive the stimulation waveforms. Some implementations may not employ a handshake signal to indicate the wireless stimulator device 922 is ready to receive the stimulation waveforms. Rather, the transmission signal may automatically transition from the configuration portion to the stimulation portion. In other implementations, the implantable wireless stimulator device 922 may provide a handshake signal to inform the MFS 902 that implantable wireless stimulator device 922 is ready to receive the stimulation portion of the transmission signal. The handshake signal, if implemented, may be provided by RX/TX module 1310 and transmitted by telemetry antenna 1332.

In some implementations, the stimulation portion of the transmission signal may also arrive at implantable wireless stimulation device through the RX antenna 1334. The transmission signal received may provide an AC source 1314. The AC source 1314 may be at the carrier frequency of the transmission signal, for example, from about 300 MHz to about 8 GHz. The stimulation portion may be rectified and conditioned in accordance with discussions above to provide an extracted stimulation waveform. The extracted stimulation waveform may be applied to each electrode of the implantable wireless stimulator device 922. In some embodiments, the application of the stimulation waveform may be concurrent, i.e., applied to the electrodes all at once. As discussed above, the polarity of each electrode has already been set and the stimulation waveform has been applied to the electrodes in accordance with the polarity settings for the corresponding channel.

In some implementations, each channel of analog mux control 1316 is connected to a corresponding electrode and may have a reference resistor placed serially. For example, FIG. 13 shows reference resistors 1322, 1324, 1326, and 1328 in a serial connection with a matching channel. Analog mux control 1316 may additionally include a calibration resistor 1320 placed in a separate and grounded channel. The calibration resistor 1320 is in parallel with a given electrode on a particular channel. The reference resistors 1322, 1324, 1326, and 1328 as well as the calibration resistor 1320 may also be known as sensing resistors 718. These resistors may sense an electrical parameter in a given channel, as discussed below.

In some configurations, an analog controlled carrier modulator may receive a differential voltage that is used to determine the carrier frequency that should be generated. The generated carrier frequency may be proportional to the differential voltage. An example analog controlled carrier modulator is VCO 733.

In one configuration, the carrier frequency may indicate an absolute voltage, measured in terms of the relative difference from a pre-determined and known voltage. For example, the differential voltage may be the difference between a voltage across a reference resistor connected to a channel under measurement and a standard voltage. The differential voltage may be the difference between a voltage across calibration resistor 1320 and the standard voltage. One example standard voltage may be the ground.

In another configuration, the carrier frequency may reveal an impedance characteristic of a given channel. For example, the differential voltage may be the difference between the voltage at the electrode connected to the channel under measurement and a voltage across the reference resistor in series. Because of the serial connection, a comparison of the voltage across the reference resistor and the voltage at the electrode would indicate the impedance of the underlying tissue being stimulated relative to the impedance of the reference resistor. As the reference resistor's impedance is known, the impedance of the underlying tissue being stimulated may be inferred based on the resulting carrier frequency.

For example, the differential voltage may be the difference between a voltage at the calibration resistor and a voltage across the reference resistor. Because the calibration resistor is placed in parallel to a given channel, the voltage at the calibration is substantially the same as the voltage at the given channel. Because the reference resistor is in a serial connection with the given channel, the voltage at the reference resistor is a part of the voltage across the given channel. Thus, the difference between the voltage at the calibration resistor and the voltage across the reference resistor correspond to the voltage drop at the electrode. Hence, the voltage at the electrode may be inferred based on the voltage difference.

In yet another configuration, the carrier frequency may provide a reading of a current. For example, if the voltage over reference resistor 1322 has been measured, as discussed above, the current going through reference resistor and the corresponding channel may be inferred by dividing the measured voltage by the impedance of reference resistor 1322.

Many variations may exist in accordance with the specifically disclosed examples above. The examples and their variations may sense one or more electrical parameters concurrently and may use the concurrently sensed electrical parameters to drive an analog controlled modulator device. The resulting carrier frequency varies with the differential of the concurrent measurements. The telemetry feedback signal may include a signal at the resulting carrier frequency.

The MFS 902 may determine the carrier frequency variation by demodulating at a fixed frequency and measure phase shift accumulation caused by the carrier frequency variation. Generally, a few cycles of RF waves at the resulting carrier frequency may be sufficient to resolve the underlying carrier frequency variation. The determined variation may indicate an operation characteristic of the implantable wireless stimulator device 922. The operation characteristics may include an impedance, a power, a voltage, a current, etc. The operation characteristics may be associated with an individual channel. Therefore, the sensing and carrier frequency modulation may be channel specific and applied to one channel at a given time. Consequently, the telemetry feedback signal may be time shared by the various channels of the implantable wireless stimulator device 922.

In one configuration, the analog MUX 1318 may be used by the controller module 1312 to select a particular channel in a time-sharing scheme. The sensed information for the particular channel, for example, in the form of a carrier frequency modulation, may be routed to RX/TX module 1310. Thereafter, RX/TX module 1310 transmits, through the telemetry antenna 1332, to the MFS 902, the telemetry feedback encoding the sensed information for the particular channel.

Some implementations may include an application-specific integrated circuit (ASIC) chip on the wireless stimulator device for processing input signal and interfacing with the implanted electrodes. The ASIC chip may be coupled to antenna(s) to receive the input signal from an external controller. The ASIC chip may harvest RF power from the received input signal to power the ASIC chip and the electrodes. The ASIC chip may also extract polarity setting information from the received input signal and use such information to set the polarity for electrode interfaces. Moreover, the ASIC chip may extract waveform parameters from the received input signal and use such information to create electrical impulses for stimulating excitable tissues through the electrodes. In particular, the ASIC chip may include a current steering feature to mirror currents to each electrode with evenness while maintaining a compact chip size.

Figure 14:
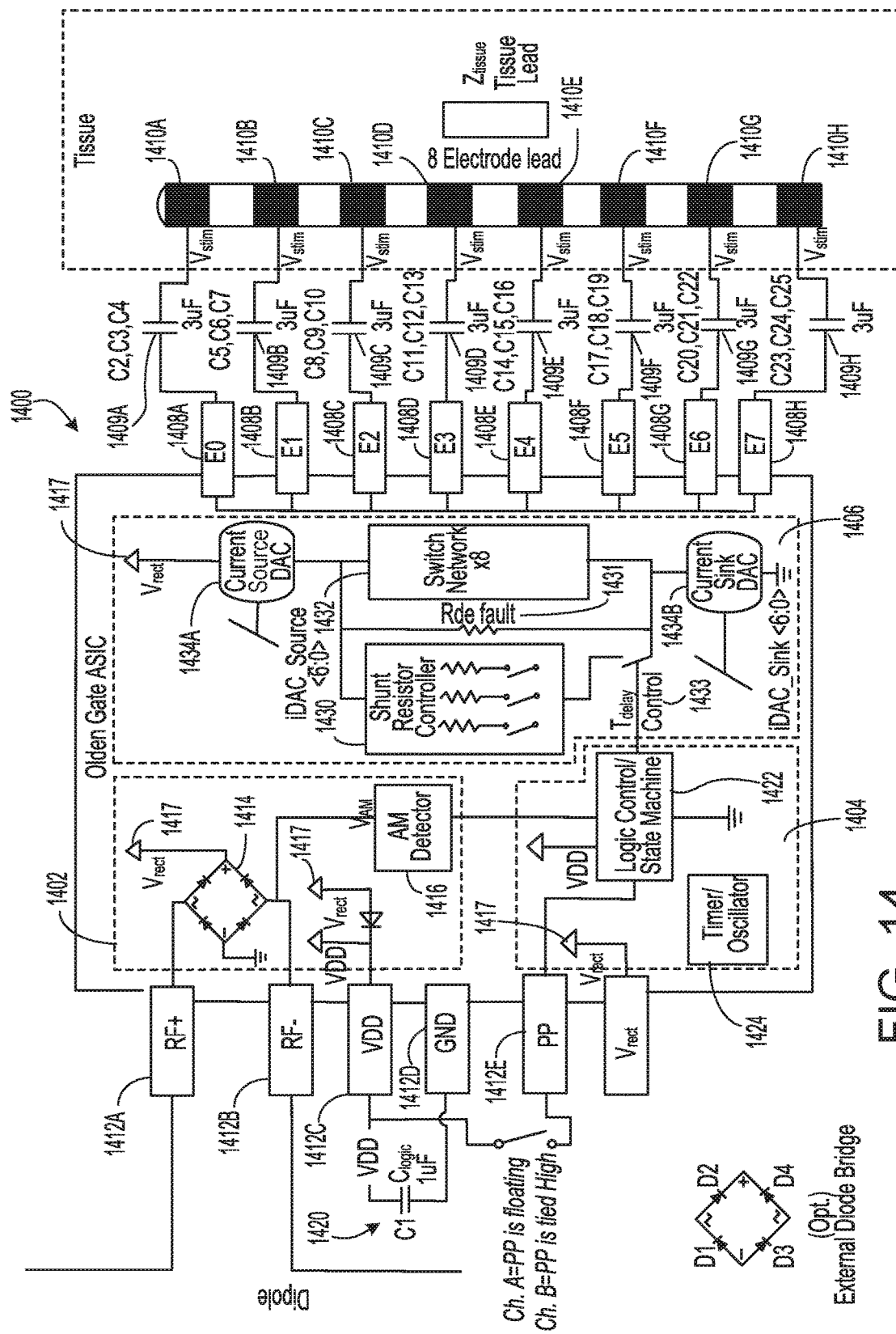
FIG. 14 is a diagram of an example application-specific integrated circuit (ASIC) chip for implantable use.

FIG. 14 is a diagram of an example of ASIC chip 1400 for implantable use. Chip 1400 may be fabricated based on a 0.6 um, double poly process utilizing High Value resistors, Schottky diodes and High Voltage Transistors. In some implementations, chip 1400 can be fabricated at a width of 0.5 mm for fitting into, for example, an 18 Gauge needle. In these implementations, chip 1400 can have a length-width ratio of up to 10 to 1. Chip 1400 can be coupled to, for example, either four (4) or eight (8) platinum-iridium electrodes that deliver electrical impulses to tissue.

Chip 1400 includes RF to DC rectifying circuit 1402, a logic control circuit 1404, and a driving circuit 1406. RF to DC rectifying circuit 1402 is coupled to differential antennas 1412A and 1412B. An RF input signal can be received at the differential antennas and then rectified to have the amplitude detected. The rectified signal may provide power for the chip 1400. Thereafter, logic control circuit 1404 may extract waveform parameters from the amplitude detected signal. Subsequently, logic control circuit 1404 may generate electrical impulses according to the extracted waveform parameters and solely based on the extracted electric power. The generated electrical impulses may then be provided to the driving circuit 1406, which includes charge balancing and current mirroring circuits. Driving circuit 1406 is coupled to electrode interfaces 1408A to 1408H, each coupled to a respective electrical load 1409A through 1409H. The electrical impulses are subsequently delivered to each electrode, namely 1410A through 1410H.

In this diagram, a diode bridge circuit 1414 is included to provide full-wave rectification to the input signal received in differential form from differential antennas 1412A and 1412B. Full-wave rectification may utilize both the positive and negative portions of the RF input signal as received at differential antennas 1412A and 1412B.

In some implementations, a dipole antenna in a differential configuration may be embedded into a wireless implantable stimulator device. The dipole antenna receives power, serial communication, and stimulus waveforms from an external transmitter placed outside the patient's body. The dipole antenna is connected directly to a flexible circuit board embedded within the implantable stimulator device that contains discrete components and chip 1400. Chip 1400 can include wireless serial command receiver with up to eight channel multiplexing functionality.

The rectification may provide power to remaining portions of chip 1400. In some instances, VDD circuit 1418 and ground circuit 1419 are coupled to capacitor C1 1420 to provide stored charges. The stored charges may generally power chip 1400. In some implementations, a diode may be used to supply the VDD logic supply from Vrect. If chip 1400 is active and the voltage VDD dips below 1.8V, chip 1400 may enter into a "VDD low voltage recovery" mode. In this state any/all high side drivers will be temporarily over ridden to high impedance state (Hi-Z) and all low side drivers will be Hi-Z. Once VDD returns t6 above 3.0V state and in the running mode the drivers would return to their previously programmed state.

Output from rectifying circuit 1402 is coupled to the logic control circuit 1404. As depicted, logic control circuit 1404 may include logic control/state machine 1422 and timer/oscillator 1424. Logic control/state machine 1422 may be coupled to channel selector 1426.

The received RF input signal may contain waveform parameters for electrical impulses to stimulate tissues. The received RF input signal may contain polarity setting information for setting the interface for each electrode.

Figure 15:
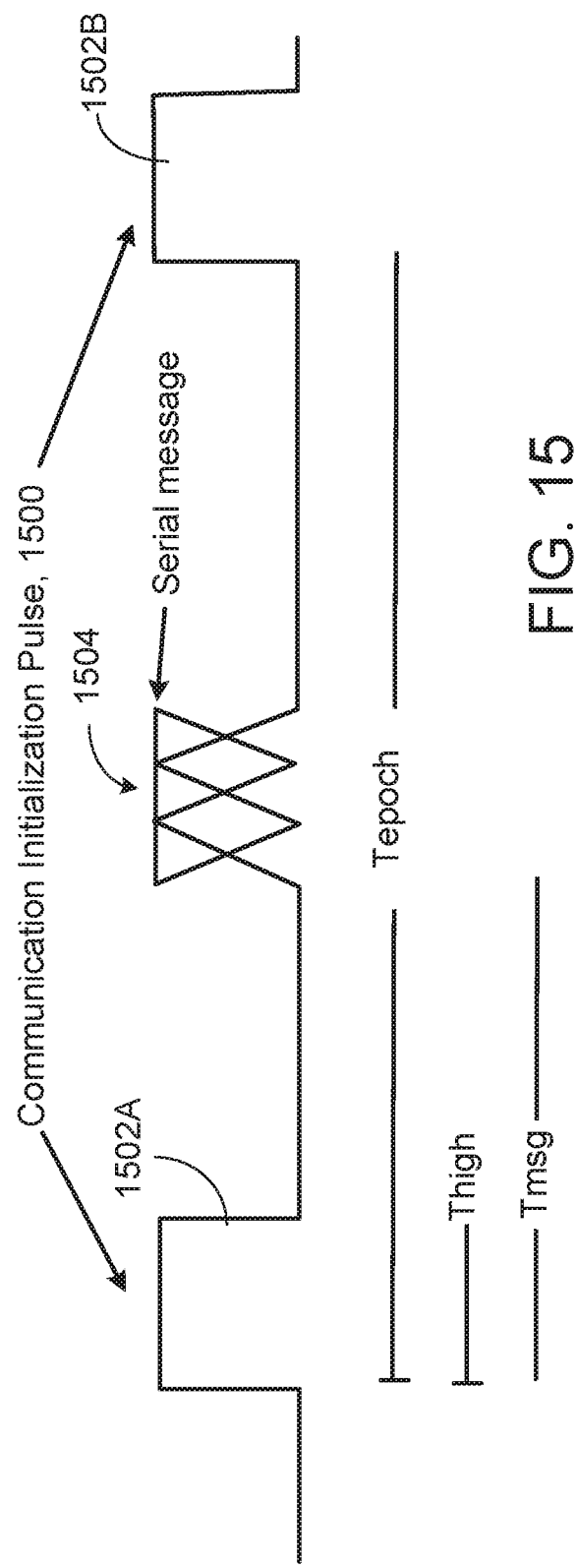
FIG. 15 shows an example sequence during operation of the ASIC chip shown in FIG. 14.

Referring to FIG. 15, a sequence diagram during operation of the chip 1400 is shown. Specifically, the pulse sequence 1500 includes segments of pulses. Each segment may last an epoch time (depicted as $T_{epoch}$). Each segment may include two portions, namely an initial portion and a subsequent stimulation portion. In more detail, the initial portion refers to the portion in which electrical power contained in the RF input signal is harvested and electrical charges are pumped into capacitor C1 1420. The initial portion may last a period marked as Thigh. The initial portion may be referred to as the communication initialization pulses 1502A and 1502B. The stimulation portion corresponds to portion 1504 and may contain a serial message encoding waveform parameters for electrical impulses and polarity setting information for the electrode interfaces. In some instances, portion 1504 may be present in the first segment of sequence 1500 to configure electrical impulses and polarity setting. Absent a power-on reset event, the configuration information of waveform parameters and polarity setting may be fixed once the initialization is completed.

Chip 1400 may tolerate serial messages embedded between power bursts. For example, the transmitter may initiate a serial communication message by sending a 2 ms "Communication Initialization Pulse", CIP, ($T_{high}$) followed by a 2 ms period of no power transmission ($T_{msg}-T_{high}$). In this example, data transmission may immediately follow this 2 ms delay and starts at time $T_{msg}$. Bit timing calibration may be performed by measuring the length of the header byte in the transmitted data stream.

In some implementations, serial data may use a format based on the IrDA SIR format. This coding format sends a pulse where the bit to be sent is a '0'. During bit times where the bit is set to "1," no pulse may be sent. Each pulse may be as short as 3/16ths of a bit time however this width can be adjusted if necessary. This format may require less power and therefore can allow serial data transmission to operate at lower baud rates.

In an example serial data communication, data can be transmitted asynchronously as bytes with 1 start and 1 stop bit (e.g. 8-n-1 format carries the same overhead to RS-232 with 10 bits transmitted but only 8 of the 10 bits carry data while the other 2 bits are protocol overhead). The LSB may be the first data bit transmitted. This adds up to 70 bits total transmitted for 7 bytes of data. Ten of these bits are protocol overhead and 60 of these bits are available to carry data. In this example, there is no additional delay between bytes, the data stream is continuous.

In the example, the serial baud rate is 19200. Serial messages can be of a fixed length of 7 bytes, including a header byte, five payload bytes, and a checksum byte. Payload bytes may generally encode the polarity setting for each electrode interface, the electrode drivers to use for each electrode, the amplitude level for each electrode driver, etc. The checksum byte generally helps ensuring message integrity.

The header byte is used to identify the start of a data message. In some implementations, it can be preset to the value 0xAA. In these implementations, the header byte can be discarded until a correct header byte is received. The header may also be used to calibrate the internal oscillator, which is powered by wireless energy stored on VDD. Some implementations may provide a unique structure of on-off-on-off-on-off-on-off-on-off for the 10-bit sequence as timing markers at regular (104 µs between transmissions) intervals.

In some implementations, the header may include the address of the selected electrode array. For example, Bit 7 of Byte 1 can be the Lead Address to distinguish between one of two possible electrode arrays is the message intended. An electrode array may only implement messages that match its lead address assigned. If a lead of channel A receives a message that is intended for channel B, the state machine may reject the new message and maintain the previously stored register contents. In this example, each electrode array can have an address of 0 or 1 that can be determined by pin strapping during manufacture of the lead.

Returning to FIG. 14, in some implementations, AM detector 1416 may output logic zero when RF power is received. In some implementations, pre-amplification of low voltage data signals or limiting of high voltage data signals may extend the operational range of the AM detector 1416. As such, signals 100 mV or greater will be detected. AM detector 1416 may decode serial streams that are transmitted at 19200 Baud. The AM detector 1416 input may be internal to chip 1400 and characterized for use at high frequencies (869-915 MHz).

AM detector 1416 may generally process rectified signals within a nominal range from between 50 mVpp to 15 Vpp power supply levels (peak to peak). AM detector 1416 may include a preamp to clamp higher swing signals without output collapsing or folding down. The preamp should have sufficient gain and low offset to resolve 100 m Vpp data signals.

AM detector 1416 may detect serial data encoded using IrDA (SIR) formatting. The serial data receiver may be included in AM detector 1416 and may convert the data from a serial format into a parallel format. Operations of the serial data receiver hardware may be controlled by a clock signal, which runs at a multiple of the data rate. In some implementations, the receiver can test the state of the incoming signal on each clock pulse to search the start bit. If the apparent start bit is valid, then the bit signals the start of a new character. If not, the bit is considered a spurious pulse or power pulse and is ignored. After waiting a further bit time, the state of the line is again sampled and the resulting level clocked into a shift register.

After the required number of bit periods for the character length have elapsed, the contents of the shift register are made available to the receiving system. The serial data receiver has no shared timing system with the transmitter apart from the communication signal.

Serial data receiver on chip 1400 may receive and buffer seven (7) eight-bit words. The data contained in the words shall be used to program the control registers in the receiver IC LMI927 if a checksum match is successful. The data will be ignored if a checksum match is unsuccessful and the receiver will continue to listen for valid data. The serial data receiver will reset and prepare to receive a new word if a received byte does not meet IrDA (SIR) framing parameters. This will allow the serial receiver to quickly reset after being falsely activated by reception of a spurious signal or a stim power pulse. The serial data receiver will not have to wait to fully receive all words if any individual byte does not meet timing parameters.

Chip 1400 may remain in an un-configured state (all high-side outputs are high-Z, low-side outputs are in triode mode) until a valid set of serial data is received. Notably, in some implementations, the serial receiver may be not be operational if the Device Lock bit is set.

Logic control/state machine 1422 may be synchronized by timer/oscillator 1424. The synchronization may enable logic control/state machine 1422 to extract and decode waveform parameters as well as polarity setting information from portion 1504. Logic control/state machine 1422 may then create one or more electrical impulses according to the waveform parameters. The Logic control/state machine 1422 may also set polarities of electrode interfaces 1408A to 1408H according to the extracted polarity setting information.

The output of Logic Control/State Machine 1422 may be coupled to driving circuit 1406 which includes features of charge balancing, shunt resistors, and current mirroring. In particular, driving circuit 1406 includes shunt resistor controller 1430 constructed to couple a shunt resistor to switch network 1432. The coupling can enhance default resistor 1431 through delay controller 1433. The delay controller may insert a corresponding shunt resistor to the circuit including the stimulating electrode at the end of an electrical impulse to reduce the amount of leakage current.

Some implementations may incorporate a variable shunt resistor to control the discharge of the stimulus pulse from the DC-Blocking capacitors. In these implementations, the initial serial commands contain instructions for the set value for the shunt resistor. For example, the operator may select between four (4) different settings. The internal shunts are configured so that during a stimulus pulse they are off, and after a pulse they are engaged.

The engagement of the resistors can be delayed following application of the electrical impulse. The timer is to delay the onset of the discharge of the DC Blocking capacitors. The timer may be initialized during the stimulus pulse and it starts its delay at the end of the stimulus phase. The delay has a fixed duration and may be independent of the stimulus amplitude, repetition rate, and pulse width.

In some implementations, the stimulating electrical impulse is delivered to a particular electrode through switch network 1432. To deliver electrical impulses at both polarities, the switch network is coupled to current source DAC 1434A and current sink DAC 1434B. As depicted, current source DAC 1434A includes a 7-bit dynamic range and is coupled to the rectifying voltage Vrect 1417. Current source DAC 1434A is invoked with the polarity of the connected electrode set as positive. Similarly, current source DAC 1434A includes a 7-bit dynamic range. Current sink DAC 1434B is invoked with the polarity of the connected electrode set as negative. Current source DAC 1434A and current sink DAC 1434B are complementary. Current source DAC 1434A and current sink DAC 1434B both include current mirrors that can function to produce a copy of the current in one device, for example, the device that generates voltage Vrect 1417, by replicating the current in another device, for example, current source DAC 1434A or current sink DAC 1434B. A current mirror generally has a relatively high output resistance which helps to keep the output current constant regardless of load conditions. Another feature of the current mirror is a relatively low input resistance which helps to keep the input current constant regardless of drive conditions.

Chip 1400 may include a supervisory Power On Reset (POR) circuit designed to keep the device in reset until the system voltage has reached the proper level and stabilized. The POR circuit also operates as protection from brownout conditions when the supply voltage drops below a minimum operating level. The POR circuit design is such that it incorporates appropriate hysteresis between reset and enable levels to prevent start up inrush currents from causing the device to reset during normal operating power-up conditions. The POR circuit performs as needed to maintain proper chip functionality under all power fluctuation conditions including high-speed transients and slow rate of change voltage conditions. If required, the POR circuit can incorporate a watchdog timer tick event to ensure proper operation of the chip 1400.

As depicted in FIG. 14, each electrode interface is coupled to a respective capacitor 1409A through 1409H. These capacitors are placed in series for the purpose of DC blocking. The capacitors are last in the signal chain before the stimulation electrical impulses are delivered to the electrodes. In some implementations, the nominal series capacitance may be 3.0/µF at each electrode. Each capacitor in turn couples to a respective electrode 1410A through 1410H on an 8-electrode stimulator device. As noted, chip 1400 may be coupled to 8 electrode outputs. Each electrode output can be set to either sourcing, sinking or Hi-Z.

Figure 16A:
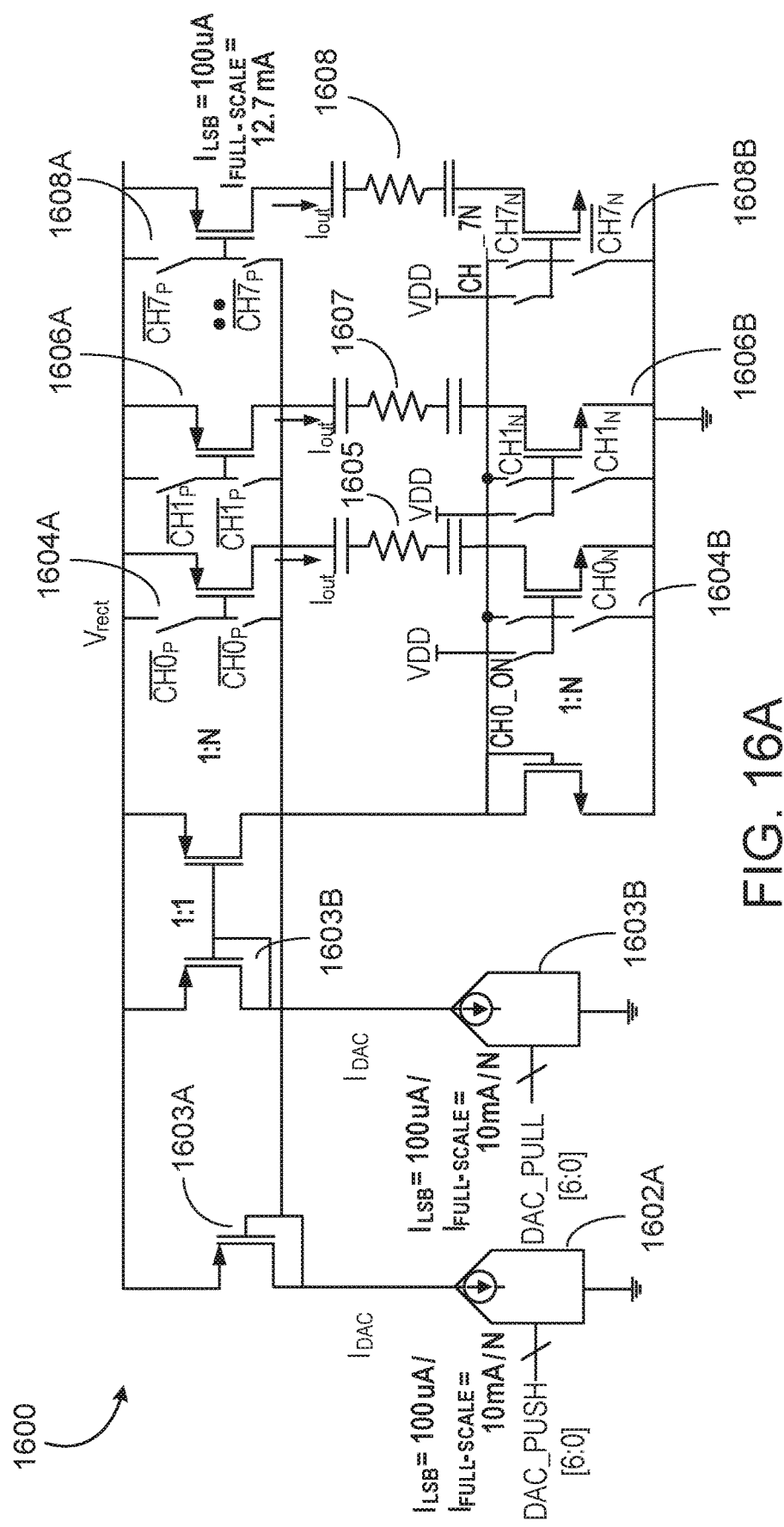
FIG. 16A shows an example current steering feature for the ASIC chip shown in FIG. 14.

Referring to FIG. 16A, an example digital-to-analog mirror is shown for chip 1400. The example highlights a current mirroring feature. Generally, multiple DACs with individually addressable and controllable current codes would increase ASIC's register space and design complexity and die area. On the other hand, having fewer DACs than available channels may require coulomb counting to limit the current through individual channels. With few DAC channels than the electrodes, the current through individual electrodes may increase for lower impedance channels.

In some implementations, a single current-steering DAC with a scaled-down least significant bit (LSB) current value is used to generate a master bias current. In these implementations, no current may be wasted in the current mirrors. After the master bias current is generated, the DAC current is then mirrored to individual electrodes with a current mirror ratio of 1:N. Here, mirrored to individual electrodes generally refers to connected via current mirrors to individual electrodes. N can be selected based on current-steering DAC matching requirements. For example, N can be in the range of 10. The LSB size of the individual electrodes may be 100 uA. With 7-bits, full dynamic range of the driving current can be up to 12.7 mA.

The implementation depicted in FIG. 16A shows a dual-DAC approach with mirrored current sources across eight (8) electrodes. Transistor gate 1603A is a replicate of transistor gate 1603B in the 1:1 transistor mirror. Digital to Analog Conversion (DAC) circuit 1602A represents a push DAC and may correspond to a current sink. Meanwhile, DAC 1602B represents a pull DAC and may correspond to a current source. Logically, DAC 1602A and DAC 1602B may respectively correspond to DAC 1434A and DAC 1434B as depicted in FIG. 14. To reduce current mirror mismatches and wasted current, an N-side, current-sink DAC is used for this application. In this configuration, individual channels are enabled with complementary signals. Specifically, channel 0 is enabled by complementary transistors 1604A (for CH0 positive) and 1604B (for CH0 negative). Transistor gate 1604A is coupled to Vrect 1417 while transistor gate 1604B is coupled to VDD 1418. Circuit 1605 represents the tissue load on channel 0 as well as DC blocking capacitors. In some implementations, the tissue load of channel 0 may include a capacitive component in addition to the resistance component. Likewise, complementary transistors 1606A and 1606B respectively represent the positive and negative polarity arrangements for driving tissue load 1607 for channel 1. This implementation depicts an 8-side, current-sink DAC configuration in which the current mirroring is replicated for each channel of the 8-channel electrode lead coupled to. For example, channel 7 driving arrangements are represented by complementary transistors 1608A and 1608B as well as tissue load 1608, as shown in FIG. 16A. Notably, in this N-side implementation, three states can be configured for each of the current sinks, namely, controlled (mirrored) current sink mode, a cutoff device (off mode), and turned-on device as a triode mode switch. As depicted, each channel further includes an ON switch. For example channel 0 includes a CH0_ON switch, while channel 1 and channel 7 respectively include CH1_ON and CH7_ON switches.

Figure 16B:
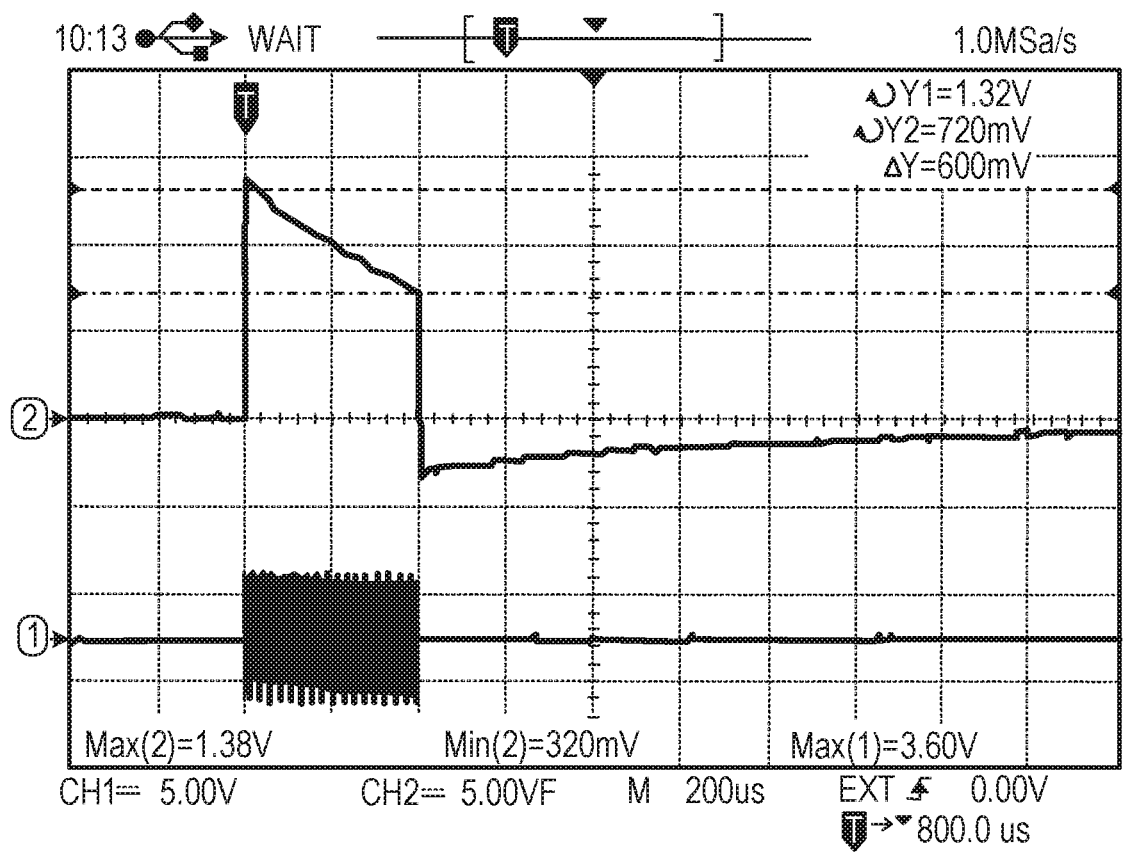
FIG. 16B shows example waveforms simulated based on the depicted ASIC chip model.

Based on this model, a variety of electrical signal parameters can be modeled before an ASIC chip is fabricated. In one example, denoting stimulating waveform after rectification as Vstim, FIG. 16B shows the expected Vstim waveform (on channel 1) and RF input signal (on channel 2). As demonstrated, a great deal of detailed performance can be simulated during the design stage.

Figure 17:
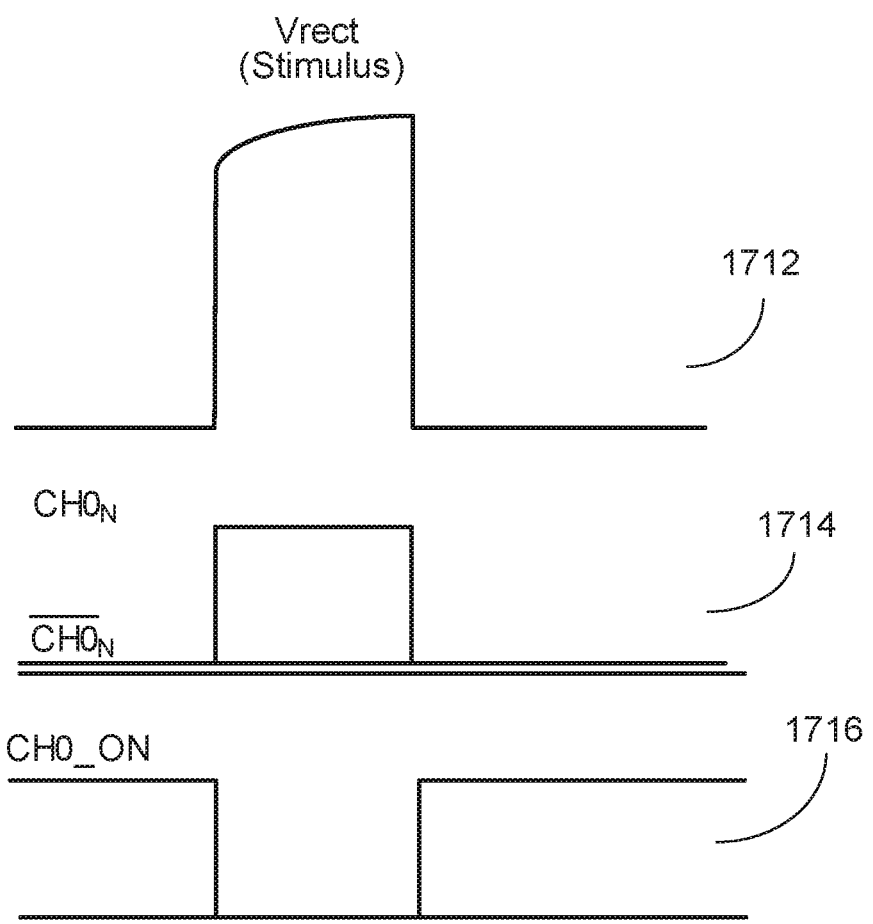
FIG. 17 shows example waveforms at various points in an ASIC chip with the current steering feature.

FIG. 17 provides an example timing of waveforms in the above implementation. Trace 1712 shows the stimulation portion of a rectified RF input signal as seen on switch CH0$_N$, while trace 1714A shows the waveform seen on switch $\overline{CH0}_N$ and trace 1714B shows the waveform seen on switch CH0_ON. The ON resistance of the triode mode may not be critical, since it is on during reverse discharge, and not during stimulus mode.

Current steering as implemented (one current source and eight mirrors) may limit the charge per phase such that electrical impulses are applied for stimulation within safety ranges. In some implementations, the external transmitter may prescribe a limit on pulse width and the serial-written current level of the amplitude. With these parameters prescribed (or capped), a patient user is prevented from requesting an unsafe charge per phase because the patient user has limited parameter selection choices. In these implementations, when the stimulus portion is not present in the rectified RF input signal, the current DACs may be inactive.

To prevent a single electrode from sourcing or sinking more than the acceptable charge per phase, a current control approach can be used for both high and low sides. In the current steering stimulus approach, high side is a single current source DAC connected to Vrect voltage with current mirrors for each electrode. The low side is a current sink DAC. Each current steering DAC may include a 7-bit converter. Because a LSB corresponds to 100 μA, the maximum current can be limited to 12.7 mA per electrode. The master current reference for the DAC can be derived from Vrect. Following-current mirrors can be taken from Vrect. A similar approach on the low side can be used to prevent a single electrode from sinking too much charge.

A number of implementations have been described. Nevertheless, it will be understood that various modifications may be made. Accordingly, other implementations are within the scope of the following claims.

What is claimed is:

1. An integrated circuit for an implantable wirelessly powered device for implantation in a patient's body, the integrated circuit comprising:
   a radio-frequency (RF) to direct current (DC) rectifying circuit coupled to one or more antennas of the implantable wirelessly powered device, the rectifying circuit configured to:
      rectify an input RF signal received at the one or more antennas and from an external controller through non-inductive coupling; and
      extract DC electrical energy from the input RF signal;
   a logic control circuit connected to the rectifying circuit and a driving circuit, the logic control circuit configured to:
      extract waveform parameters from the rectified input RF signal;
      generate a current for the driving circuit using the extracted DC electrical energy;
      generate one or more electrical impulses according to the extracted waveform parameters; and
   the driving circuit coupled to one or more electrodes and further comprises current mirrors, a shunt resistor controller, and a switch network, the driving circuit configured to:
      deliver the one or more electrical impulses through the one or more electrodes to modulate neural tissue within the patient's body,
   wherein the switch network is coupled to the current mirrors for delivering the one or more electrical impulses to the one or more electrodes, and wherein the shunt resistor controller is configured to couple a shunt resistor to the switch network at an end of an electrical impulse.

2. The integrated circuit of claim 1, wherein the one or more antennas comprise one or more patch antennas, one or more slot antennas, or one or more dipole antennas.

3. The integrated circuit of claim 1, wherein the one or more antennas comprise one or more differential dipole antennas.

4. The integrated circuit of claim 1, wherein the logic control circuit is further configured to set polarity state for each electrode during a communication initialization pulse of the input RF signal.

5. The integrated circuit of claim 1, wherein the logic control circuit is configured to generate the one or more electrical impulses that result in a substantially zero net charge at the one or more electrodes.

6. The integrated circuit of claim 1, wherein the driving circuit comprises: a current source digital to analog circuit (DAC), and a current sink digital to analog circuit (DAC), the current source DAC and the current sink DAC being complementary to each other and both being connected to each electrode via current mirrors.

7. The integrated circuit of claim 1, wherein the driving circuit comprises: a switch network configured to control a polarity state for each electrode.

8. The integrated circuit of claim 1, wherein the driving circuit comprises:
   a variable shunt resistor adapted to reduce a ripple on the electrode connected thereto when the electrical impulse has just ended.

9. The integrated circuit of claim 1, further comprising: a discharge delay timer to delay an onset of discharge of capacitors coupled to each of the electrodes.

10. The integrated circuit of claim 1, wherein the rectifying circuit comprises a diode bridge.

11. The integrated circuit of claim 1, wherein the rectifying circuit comprises: an amplitude modulation detection circuit to extract the electrical energy from the rectified input RF signal.

12. An implantable wirelessly powered device to modulate neural tissue within a patient's body, comprising:
   one or more electrodes;
   one or more antennas; and
   an integrated circuit, the integrated circuit comprising:
      a radio-frequency (RF) to direct current (DC) rectifying circuit coupled to the one or more antennas, the rectifying circuit configured to:
         rectify an input RF signal received at the one or more antennas and from an external controller through non-inductive coupling; and
         extract DC electrical energy from the input RF signal; and
      a logic control circuit connected to the rectifying circuit and a driving circuit, the logic control circuit configured to:
         extract waveform parameters from the rectified input RF signal;
         generate a current for the driving circuit using the extracted DC electrical energy; and
         generate one or more electrical impulses according to the extracted waveform parameters,
      wherein the driving circuit is coupled to the one or more electrodes and further comprises current mirrors, a shunt resistor controller, and a switch network, the driving circuit configured to:
  deliver the one or more electrical impulses through the one or more electrodes to modulate neural tissue within the patient's body,
  wherein the switch network is coupled to the current mirrors for delivering the one or more electrical impulses to the one or more electrodes, and wherein the shunt resistor controller is configured to couple a shunt resistor to the switch network at an end of an electrical impulse.

13. The implantable wirelessly powered device of claim 12, wherein the one or more antennas are configured to receive the input RF signal through non-inductive coupling, and wherein the implantable wirelessly powered device does not include a battery.

14. The implantable wirelessly powered device of claim 12, wherein the one or more antennas comprise one or more patch antennas, one or more slot antennas, or one or more dipole antennas.

15. The implantable wirelessly powered device of claim 12, wherein the logic control circuit is further configured to set polarity state for each electrode during a communication initialization pulse of the input RF signal.

16. The implantable wirelessly powered device of claim 12, wherein the logic control circuit is configured to generate the one or more electrical impulses that result in a substantially zero net charge at the one or more electrodes.

17. A system configured to modulate neural tissue within a patient's body, comprising:
  an external controller; and
  an implantable wirelessly powered device, comprising:
    one or more electrodes;
    one or more antennas; and
    an integrated circuit, the integrated circuit comprising:
      a radio-frequency (RF) to direct current (DC) rectifying circuit coupled to the one or more antennas, the rectifying circuit configured to:
        rectify an input RF signal received at the one or more antennas from the external controller through non-inductive coupling; and
        extract DC electrical energy from the input RF signal; and
      a logic control circuit connected to the rectifying circuit and a driving circuit, the logic control circuit configured to:
        extract waveform parameters from the rectified input RF signal;
        generate a current for the driving circuit using the extracted DC electrical energy; and
        generate one or more electrical impulses according to the extracted waveform parameters,
      wherein the driving circuit is coupled to the one or more electrodes and further comprises current mirrors, a shunt resistor controller, and a switch network, the driving circuit configured to:
        deliver the one or more electrical impulses through the one or more electrodes to modulate neural tissue within the patient's body,
        wherein the switch network is coupled to the current mirrors for delivering the one or more electrical impulses to the one or more electrodes, and wherein the shunt resistor controller is configured to couple a shunt resistor to the switch network at an end of an electrical impulse.

18. The system of claim 17 wherein the one or more antennas are configured to receive the input RF signal through non-inductive coupling, and wherein the implantable wirelessly powered device does not include a battery.

19. The system of claim 17 wherein the logic control circuit is configured to generate the one or more electrical impulses that result in a substantially zero net charge at the one or more electrodes.

* * * * *